(12) United States Patent
McLaren et al.

(10) Patent No.: US 11,058,711 B2
(45) Date of Patent: Jul. 13, 2021

(54) USE OF RESISTANT POTATO STARCH AS A PREBIOTIC TO MODIFY MICROBIOTA

(71) Applicant: McPharma Biotech Inc., Carberry (CA)

(72) Inventors: Derek McLaren, Carberry (CA); Earl McLaren, Carberry (CA)

(73) Assignee: McPharma Biotech Inc., Carberry (CA)

( * ) Notice: Subject to any disclaimer, the term of this patent is extended or adjusted under 35 U.S.C. 154(b) by 44 days.

(21) Appl. No.: 16/301,517

(22) PCT Filed: Jul. 6, 2017

(86) PCT No.: PCT/CA2017/050817
§ 371 (c)(1),
(2) Date: Nov. 14, 2018

(87) PCT Pub. No.: WO2018/010013
PCT Pub. Date: Jan. 18, 2018

(65) Prior Publication Data
US 2019/0224230 A1    Jul. 25, 2019

Related U.S. Application Data

(60) Provisional application No. 62/362,760, filed on Jul. 15, 2016, provisional application No. 62/396,543, filed on Sep. 19, 2016.

(51) Int. Cl.
| | |
|---|---|
| A61K 31/718 | (2006.01) |
| A61K 35/745 | (2015.01) |
| A61P 1/14 | (2006.01) |
| C08L 3/02 | (2006.01) |
| A23L 33/105 | (2016.01) |
| A23L 33/135 | (2016.01) |
| A61K 36/81 | (2006.01) |

(52) U.S. Cl.
CPC .......... *A61K 31/718* (2013.01); *A23L 33/105* (2016.08); *A23L 33/135* (2016.08); *A61K 35/745* (2013.01); *A61K 36/81* (2013.01); *A61P 1/14* (2018.01); *C08L 3/02* (2013.01); *A23V 2002/00* (2013.01); *A23V 2200/3202* (2013.01); *A23V 2200/3204* (2013.01); *A23V 2250/21* (2013.01); *A23V 2250/5118* (2013.01); *A23Y 2300/19* (2013.01); *A23Y 2300/25* (2013.01); *A23Y 2300/55* (2013.01); *A23Y 2300/59* (2013.01); *Y02A 50/30* (2018.01)

(58) Field of Classification Search
CPC combination set(s) only.
See application file for complete search history.

(56) References Cited

FOREIGN PATENT DOCUMENTS

| | | |
|---|---|---|
| EP | 2892540 | 7/2015 |
| WO | 96/08261 | 3/1996 |

OTHER PUBLICATIONS

Kleessen, B. et al., J. Anim. Sci. 1997, vol. 75, pp. 2453-2463.*
Alfa Michelle J et al: "A randomized trial to determine the impact of a disgestion resistant starch composition on the gut microbiome in older and mid-age adults" Clinical Nutrition, Churchill Livingstone, Long, GB vol. 37, No. 3, Jan. 1, 2017 pp. 797-807 ISSN: 0261-5614, COI: 10.1016/J.CLNU.2017.03.025. Retrieved from the Internet: URL:https://epo.summon.serialssolutio ns.com/2.0.0/link/0/elvHCXMwnV1 Nj9MwELUWDogLHwuCsoAGCcEBIsV2nDjH 7i67HIADLAdO1uNxUFGbom.
Schmiedl, D. et al, "Feeding Resistant Starch Affects Fecal and Cecal Microflora and Short-Chain Fatty Acids n Rats", Journal of Animal Science (1997), 75:2453-2462.
Le Blay, G. et al, "Enhanceemnet of butyrate production in the rat caecocolonic tract by long-term ingestion of resistant potato starch", British Journal of Nutrition (1999), 82:419-416.
Nugent, A.P. Heath properties of resistant starch, Nutrition Bulletin (2005), 30:27-54.
Cummings, J.H. et al, "Digestion and physiological properties of resistant starch in the human large bowel", British Journal of Nutrition (1996), 75:733-747.

* cited by examiner

*Primary Examiner* — Heidi Reese
(74) *Attorney, Agent, or Firm* — Michael R. Williams; Ryan W. Dupuis; Ade & Company Inc.

(57) ABSTRACT

Consumption of resistant potato starch results in changes to the gut microbiome in elderly adults, resulting in a healthier gut microbiome profile. Furthermore, consumption of resistant potato starch stimulates an increase in *Bifidobacterium* abundance in all individuals and also reduces levels of *E. coli* and *Shigella*. Furthermore, consumption of MSPrebiotic® increased the relative ratio of butyrate in the elderly and significantly reduced the use of stool softeners in the elderly.

19 Claims, 15 Drawing Sheets

USE OF RESISTANT POTATO STARCH AS A PREBIOTIC TO MODIFY MICROBIOTA

PRIOR APPLICATION INFORMATION

The instant application claims the benefit of U.S. Provisional Patent Application Ser. No. 62/362,760, filed Jul. 15, 2016, entitled "USE OF RESISTANT STARCH AS A PREBIOTIC TO MODIFY MICROBIOTA", the contents of which are incorporated herein by reference.

The instant application also claims the benefit of U.S. Provisional Patent Application 62/396,543, filed Sep. 19, 2016, entitled "USE OF RESISTANT STARCH AS A PREBIOTIC TO MODIFY MICROBIOTA", the contents of which are incorporated herein by reference.

BACKGROUND OF THE INVENTION

Resistant starch (RS) is defined as the sum of starch and starch digestion products that are not digested in the small intestine but instead reach the large intestine as a fermentable fiber substrate. Previous research has established RS as an effective dietary prebiotic supplement to modulate intestinal function and improve systemic health in both animals and humans. In human health and disease prevention, RS has potential application in weight management, the treatment of gastrointestinal disorders, and the improvement of blood lipids, glucose tolerance and insulin sensitivity.

It is important to note however that all resistant starch is not equal. Specifically, there is exceptional diversity encountered among RS varieties. Specifically, RS varieties originating from different plant sources and/or manufactured with alternative processing technologies will possess unique physiochemical properties.

The gut microbiome represents the microbial community within the small intestine and the colon. Most of the fermentative reactions occur in the transverse and descending colon. The human body cannot digest various starches such as uncooked potato starch as it is digestion-resistant starch that can only be broken down by fermentative bacteria in the colon. A key end-product of the fermentation of RS in the colon is the short chain fatty acid (SCFA) butyrate which provides energy for the gut colonocytes. Without adequate butyrate to provide energy, the colonocytes in the colon undergo autophagia which leads to death of these human gut cells. The normal composition of the healthy human gut microbiome in excreted feces falls into five main Phyla including Firmicutes, Bacteroidetes, Actinobacteria, Proteobacteria and Verrucomicrobiota.

It is estimated that 500 to 1000 species of bacteria live in the human gut. Many of the bacteria in the digestive tract, collectively referred to as the gut microbiota, are able to break down certain nutrients such as carbohydrates that humans otherwise could not digest. Gut microorganisms benefit the host by collecting the energy from the fermentation of undigested carbohydrates and the subsequent absorption of short-chain fatty acids such as butyrate, which is metabolized by the colonic epithelium.

The general composition of the gut microbiome has been reported to change with aging whereby there is in some cases a decrease in Actinobacteria and Bacteroidetes and an increase in Firmicutes. This change in microbiome correlates with reduction in SCFA production (SCFAs produced by the gut microbiome provide at least 10% of the energy for the human body) and decreased diversity in the types of microbes present.

The gut microbiome in humans is a complex ecosystem that works in harmony with the human gastrointestinal tract providing key metabolic end-products that are essential to the health of the host (Holmes 2012, Topping 2001, Ze 2012, Belenguer 2006, Flint 2012, Cecchini 2013, Pokusaeva 2011). The microbes within the intestinal tract affect a wide range of human biologic functions including: gut integrity, immune function, bile and lipid metabolism, various organ functions (e.g. heart, liver, brain, etc) and susceptibility to infections of the gastrointestinal tract (Brown 2012, Holmes 2012, Malaguarnera, Toward 2012, Hardy 2013, Topping 2001). Holmes et al (2012) have described the host-microbe metabolic axis as " . . . a multidirectional interactive chemical communication highway . . . ". This fits with Biagi et al's (2012) description of humans as "meta-organisms" that undergo immunosenescence as they age that corresponds with gut microbiome alterations that lead to dysbiosis. The dysbiosis of the gut microbiome has been associated with illnesses such as irritable bowel syndrome (IBS), colitis, Crohn's, colorectal cancer, allergy, Coeliac and *Clostridium difficile* disease (Antharam 2013, Claesson 2011, Hardy 2013, Holmes 2012, Biagi 2012, Brown 2012). Claesson et al (2011) reported that in the 161 adults 65 years and older from the Irish Eldermet consortium that there was stability of the microbiome over a 3-month period but there were unusual phyla proportions and extreme variability in the elderly compared to younger adult controls (i.e. a high percentage of singleton operational taxonomic units (OTUs)). They reported that in the elderly cohort there was a predominance of Bacteroidetes (57%) with Firmicutes representing the second major group (40%). However, in the younger cohort the ratio was reversed with Firmicutes as the predominant phylum (51%) and Bacteroidetes at a lower level (41%). Others have also reported that the elderly have less diversity in their gut microbiome compared to younger adults (Brown 2012, Holmes 2012, Biagi 2012, Toward 2012, Claesson 2012) and this may be related to a less diverse diet (Brown 2012, Claesson 2012). Claesson (2012) suggested that as humans age, become more frail and require institutionalization, their nutritional status changes and this leads to their gut microbiome becoming significantly less diverse compared to community dwellers. Indeed, they stated: " . . . the most plausible interpretation of our data is that diet shapes the microbiota, which then affects health in older people." Biagi et al (2012) proposed that as humans age so does their microbiome and the immunesenescence observed in elderly adults is linked to a restricted diet leading to dysbiosis in the elderly microbiome. The gut dysbiosis has many effects, including a loss of integrity of the gut barrier due to apoptosis of colonocytes as a result of inadequate butyrate from which they derive their energy. There are conflicting reports regarding exactly what microbiome changes occur in the elderly but there is agreement that the gut microbiome is altered. A key question (Holmes 2012) is whether supplementation of the diet in the elderly with probiotics, prebiotics or synbiotics could correct the dysbiosis in the elderly gut microbiome, thereby improving health of the elderly.

Priebe (2002) stated that the widely used definition of probiotics is; "a live microbial feed supplement which beneficially affects the host (animal) by improving its intestinal microbial balance". In contrast, prebiotics are most often defined as; "non-digestible food ingredients that beneficially affect the host by selectively stimulating the growth and/or activity of one of a limited number of bacteria in the colon, that can improve the host health". It is unclear whether prebiotics or probiotics alone or together can correct gut microbiome dysbiosis in the elderly and whether this will manifest in clinical outcomes that improve the health and well-being of the elderly. This is further confounded by the fact that elderly residents are frequently treated with antibiotics and often have additional co-morbidities affecting overall well-being. Claessen (2012) and Dethlefsen et al (2011) clearly established that antibiotic treatment causes profound and rapid loss in gut microbiome diversity and a shift in composition. In some cases, it takes weeks for the antibiotic-shifted microbiome to return to baseline after antibiotic treatment is stopped. Trying to make sense of the gut microbiome changes in the elderly in response to prebiotic consumption can be challenging as there are multiple confounding factors.

The number of prebiotics that have been evaluated in clinical studies is limited (Toward 2012, Patel 2015) and includes: inulin, galactooligosaccharides, fructooligosaccharides, and xylooligosaccharides (Patel 2015, Toward 2012, Kleesen 1997, Delzenne 2011). There have been very few clinical studies in elderly adults to determine if digestion-resistant starch could be an effective prebiotic and whether prebiotic consumption alone is sufficient to stimulate endogenous Bifidobacteria or Lactobacilli (bacteria associated with good gut health). This is a significant consideration because if the specific bacteria targeted by prebiotics were not available in the endogenous microbiome of the elderly, then prebiotics would need to be administered along with probiotics (i.e. synbiotics) to get the desired health effect.

Furthermore, it has been postulated that the microbiome may have a role in auto-immune diseases like diabetes, rheumatoid arthritis, muscular dystrophy, multiple sclerosis and fibromyalgia. Specifically, it has been shown that individuals with autoimmune disorders have relatively unstable gut biomes with significantly decreased levels of species diversity.

It has also been theorized that an altered gut microbiota profile is associated with the obese state. Specifically, obesity is associated with phylum-level differences in the microbiota and a significantly reduced bacterial diversity.

As will be appreciated by one of skill in the art, any intervention may indirectly affect groups of the colon bacteria other than those being targeted, complicating any ability to predict the full extension of their effects.

For example, different species of Bifidobacteria are believed to exert a range of beneficial health effects, including the regulation of intestinal microbial homeostasis, the inhibition of pathogens and harmful bacteria that colonize and/or infect the gut mucosa, as well as improve the gut mucosal barrier.

Furthermore, a compound that increases Bifidobacteria counts is considered to have a "bifidogenic effect" whereas compounds that increase butyrate production are considered to have a "butyrogenic effect".

SUMMARY OF THE INVENTION

According to an aspect of the invention, there is provided a method of increasing beneficial Bifidobacteria content in the gut microbiota of an individual in need of such treatment comprising administering to said individual an effective amount of a suitable resistant potato starch on a dosage regimen.

In another aspect of the invention, there is provided a method of promoting a symbiotic gut microbiome or a more beneficial gut microbiome or a more beneficial gut microbiome profile in an individual in need of such treatment comprising administering to said individual an effective amount of a suitable resistant potato starch on a dosage regimen.

Accordingly, in some embodiments, there is provided a method of reducing Enterobacteriaceae or Proteobacteria content in the gut microbiota of an individual in need of such treatment comprising administering to said individual an effective amount of a suitable resistant potato starch on a dosage regimen.

According to an aspect of the invention, there is provided a method for increasing butyrate levels within the colon of an elderly individual comprising administering to said individual an effective amount of a suitable resistant potato starch on a dosage regimen.

DESCRIPTION OF THE PREFERRED EMBODIMENTS

Figure 1:
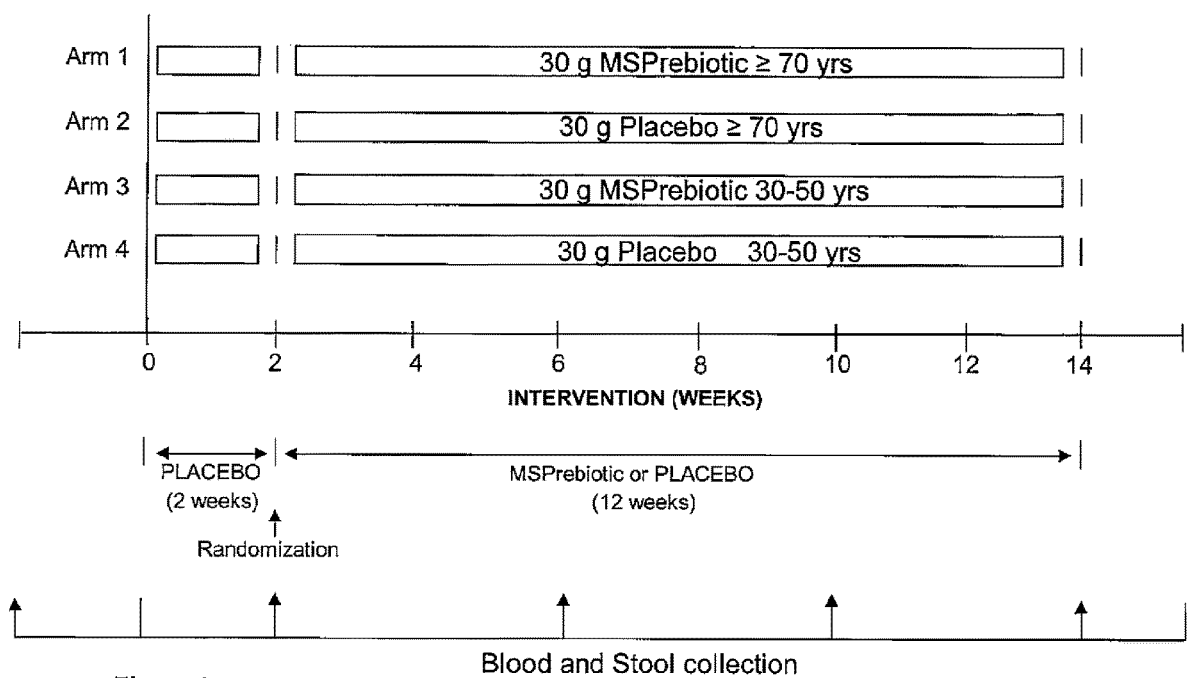
FIG. 1 provides a schematic overview of the clinical study.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

MSP Starch Products Inc, manufactures MSPrebiotic® Resistant Potato Starch, an unmodified RS type 2 starch that is a *Solanum Tuberosum* Extract preparation of food grade quality for animal and human food application. While MSPrebiotic®, which contains 7 g of fiber in 10 g of product is used in the trials and experiments discussed herein, it is important to note that as discussed herein, another suitable resistant potato starch, that is, another unmodified RS type 2 potato starch, comprising at least 60% resistant starch or at least 65% resistant starch or at least 70% resistant starch or at least 75% resistant starch or at least 80% resistant starch may be used.

The aim of this study was to determine if consumption of MSPrebiotic® over 12 weeks (after 2 weeks of placebo) would result in changes to the gut microbiome that lead to a healthier gut in elderly (i.e. adults 70 years and older) that would make it more like the gut microbiome of a younger adult population (i.e. adults between 30 to 50 years of age). In other words, if consumption of MSPrebiotic® would alter the gut microbiome profile in the elderly such that the gut microbiome profile became more similar to or more like the gut microbiome profile of the younger adult population.

The data confirm that MSPrebiotic® at 30 g/day is well tolerated and fits the criteria of a prebiotic because it stimulates an increase in *Bifidobacterium* abundance in both the elderly (ELD) and mid-age group (MID). Furthermore, consumption of MSPrebiotic® increased the relative ratio of butyrate among SCFAs in the elderly and significantly reduced the use of stool softeners in the elderly. As will be appreciated by one of skill in the art, this will also reduce the pH of the colon, which is also important for and associated with colonic health.

Gut Microbiome Changes in Adults (Young Versus Elderly) in Various Countries

Most studies have reported that as adults age they undergo immunosenescence and this is mirrored by decreased diversity in their gut microbiome and alteration in the predominant Phylum (Claesson 2011, 2012, Holmes 2012, Hardy 2013, Arumugam 2011, Toward 2012, Biagi 2012). It is unclear if the gut microbiome changes are the cause or are the result of the aging process. In addition, there appears to be geographic variation in the predominant Phylum of the gut microbiome regardless of age. In the Irish younger population (Cleeson 2011, 2012) Firmicutes was the predominant phylum (51%) closely followed by Bacteroidetes (41%), whereas in the present study with Canadian mid-age participants Firmicutes was dominant (77%) with Bacteroidetes a distant second (11%). In the Irish elderly, Bacteroidetes (57%) was the predominant phylum followed by Firmicutes (42%) whereas in the present study with Canadian elderly, the predominant phylum was Firmicutes (73%) with Bacteroidetes (14%) being the second most predominant phylum. If Claesson (2012) is correct that "diet shapes the microbiota", the differences in relative abundance of various phylum may be a reflection of different composition and diversity of the diets eaten in Ireland compared to Canada that is independent of age. Regarding the phylum relative abundances in our study, the Canadian adults cohort was more in line with the review by Biagi (2012) who indicated that clinical studies have found that in many different countries, Firmicutes is the predominant phylum (50-80%) in adults followed by Bacteroidetes (10-40%) with all other phylum combined being about 10%. The recent report by Zhernakova et al (2016) for a large Dutch cohort has abundances of Firmicutes (63.7%) and Bacteroidetes (8.1%) similar to the data for the Canadian population. Importantly, this clinical study excluded participants from enrolment if they were on or had taken antibiotics within the previous five weeks or if they took antibiotics during the study within the previous five weeks of a stool sample being collected. Thus, antibiotic consumption was not a confounding factor in this study of the human gut microbiome.

There is conflicting data on age-related changes in the dominant gut microbiota. Mariat 2009 (population not specified) and Claesson 2010 (Irish elderly) reported that the Firmicutes/Bacteroidetes ratio was lower in elderly whereas Biagi 2012 did not observe this ratio change in elderly Italians. Our data from Canadian elderly showed a slightly lower Firmicutes/Bacteroidetes ratio (5.21) in elderly compared to younger adults (7.0); however, these ratios were very different from Clasesson et al's (2011) ratios of 0.7 and 1.4, respectively and more in line with Zhernakova et al's (2016) ratio of 7.9 for the general Dutch population. Biagi's review (2012) indicated that there was general agreement in the increased facultative anaerobes (Proteobacteria) in elderly adults in various counties. Our data does support this as there was a significantly increased proportion of Proteobacteria (particularly Enterobacteriaceae, specifically the *E. coli/Shigella* group) in the Canadian elderly compared to mid-age adults at baseline. Unlike other studies, we did not observe a significant difference between elderly and mid-age Canadian adults in the abundance of the Actinobacteria Phylum or the abundance of Bifidobacteria within this Phylum at baseline.

Some of the reported variation in phylum and diversity in the published literature may be related to exclusion criteria for elderly participants, the progressive improvements in the 16S sequencing techniques and the statistical analysis methods used as well as sample collection.

Enterotypes

There are considered to be three enterotypes found in the gut microbiome of humans: Type 1, which is characterized by high levels of *Bacteroides*; Type 2 which was few *Bacteroides* but *Prevotella* are common; and Type 3 which has high levels of *Ruminococcus*.

Overall our data show that for the Canadian population studied that the mid-age cohort belonged to Enterotype 2 (as defined by Arumugam et al 2011) at baseline and this was unchanged for MID-Placebo by the end of the study whereas the MID-MSPrebiotic® cohort changed to be Enterotype 1 at the end of the study. The ELD cohort belonged to Enterotype 1 at baseline and both ELD-MSPrebiotic® and ELD-Placebo remained the same enterotype throughout the study (i.e. *Bacteroides* was predominant with *Prevotella* and *Ruminococcus* being less abundant).

Impact of Prebiotic Vs Placebo on Gut Microbiome:

MSPrebiotic® is a starch that consists of ~20% amylose (linear glucose polymer with mostly Alpha-1,4 linkages) and ~80% amylopectin (branched glucose polymer with Alpha-1,4 and Alpha-1,6 linkages) that form granules (15 to 100 microns in diameter). These MSPrebiotic® granules are not digested in the human stomach or small intestine but rather reach the colon relatively intact. The study by Nofraries et al (2007) demonstrated that long term consumption of resistant starch (raw potato starch; RPS) led to a significant increase in butyrate in the proximal colon of pigs that was not seen in pigs lacking resistant starch in their diet. Furthermore, they demonstrated that consumption of RPS resulted in improved colonic integrity and less apoptosis of colonic mucosal lymphoid tissue. This has been further substantiated by the study by Donohoe et al (2011) where colonocytes from germ-free mice were used to demonstrate how the microbiome-derived butyrate regulates energy metabolism and autophagy in the gut. Their findings clearly demonstrated that butyrate that was produced by Firmicutes was able to maintain energy homoeostasis and prevent autophagy in gut colonocytes by acting as an energy source. The effect of butyrate on colonocytes is unique as most other human cell types utilize glucose as their energy source (Topping 2001, Donohoe 2011). The review by Patel and DuPont (2015) summarized the published data supporting the value of probiotic and prebiotic supplementation to stimulate butyrate in the human colon thereby improving tight junctions, reducing bacterial translocation, and stimulating mucin synthesis, all of which are key components of ensuring integrity of the gut epithelium.

There have been a wide variety of studies with probiotics but very few with prebiotics. Furthermore, it is unclear if the synbiotic approach (prebiotics combined with probiotics) is needed. Our data demonstrate for the first time that there was a significant increase in the abundance of *Bifidobacterium* in both elderly and mid-age groups consuming MSPrebiotic® compared to placebo. *B. bifidum, B. dentium* and *B. pseudocatenulatum* were the predominant species identified at baseline. The percentage of *B. dentium* decreased with MSPrebiotic® consumption whereas the percentage of *B. pseudocatenulatum* and/or *B. ruminantium* increased significantly in the cohort taking MSPrebiotic®. This likely reflects the ability of *B. pseudocatenulatum* and *B. ruminantium* to preferentially ferment potato starch (Belenguer 2006). The percentage of *B. adolescentis* also tended, to increase in the MSPrebiotic® supplemented groups. This ability to increase levels of endogenous Bifidobacteria in mid-age and elderly individuals indicates that MSPrebiotic® could be used alone as a prebiotic supplement for nutritional interventions to prevent and counteract dysbiosis in the absence of a probiotic supplement However, in some embodiments, as discussed herein, MSPrebiotic® may be used in combination with a suitable probiotic. As will be appreciated by one of skill in the art, the probiotic may be coadministered with the resistant potato starch but not necessarily on the same dosage regimen as the resistant potato starch. That is, the probiotic may be coadministered once, twice, three times, weekly, monthly or as needed rather than daily as is the resistant potato starch, as discussed herein. Furthermore, it is important to note that coadministration does not necessarily mean simultaneous coadministration, as the probiotic may be administered before or after the daily dose of resistant potato starch.

SCFA in Stool:

There was a small but significant increase in ratio of butyrate within SCFAs for MSPrebiotic® compared to placebo in elderly. However, at baseline the relative proportions of SCFA were very different between elderly and mid-age adults. Mid-age adults had >98% propionate, <0.5% butyrate and <3% acetate. In contrast, in elderly at baseline, acetate represented about 22%, butyrate about 1.5% and propionate about 75%. Topping (2001) reported that there was a wide range in the relative amounts of the three SCFAs in published studies but generally the order of abundance was acetate>propionate>butyrate (Nofrarias 2007, Kleeson 1997, McOrist 2011). In contrast, in our study the order was propionate>acetate>butyrate. A number of factors such as transit time, absorption gradient and fluid volume affect the amount of SCFA in feces (Topping 2001). Our stool samples were made into a slurry (i.e. entire stool sample thoroughly mixed with PBS at 1:3) usually within 24 hours of collection (72 hours for samples collected from institutionalized ELD collected on the weekend) and aliquots frozen. SCFA analysis used a sample that had only been freeze-thawed one time.

Butyrate is largely utilized by the colonic epithelium as an energy source, and propionate is primarily utilized by the liver, whereas a significant amount of acetate enters systemic circulation and reaches peripheral tissues (Lin, 2012). Furthermore, it is widely agreed that colonic fermentation producing butyrate suppresses cancer cell proliferation (Malcomson, 2015). As discussed herein and is known to those of skill in the art, increased production of butyrate will also increase colon pH which is associated with and is important for colon health.

Cross-Feeding in Microbiome:

It is interesting that the increased abundance of Bifidobacteria when MSPrebiotic® was consumed was paralleled by an increase in the relative ratio of butyrate within the SCFAs in the elderly participants even though Bifidobacteria do not produce butyrate (nor do Lactobacilli). Topping (2001) reviewed a number of in vitro studies and summarized that substantially more butyrate was formed from potato starch and other RS2 starches than from RS3 and maize starch. Wang et al (1999) tested a wide variety of bacteria and reported that Bifidobacteria were among the bacteria with the highest growth and degradation rates for amylopectin (digestion-resistant starch). None of the *Lactobacillus* or Proteobacteria tested and only limited Firmicutes could utilize resistant starch (Wang 1999).

The published data regarding "cross-feeding" (Topping 2001, Ze 2012, Belenguer 2006, Flint 2012, Cecchini 2013, Pokusaeva 2011) indicate that when resistant starch is broken down (primarily by Actinobacteria (e.g. *Bifidobacterium*)) that the end products, acetate and lactate, can then act as substrates for butyrate-producing Firmicutes. A plausible relationship between the observed increase in *Bifidobacterium* abundance and increase in butyrate may be related to cross-feeding as summarized in FIG. 5. *Ruminococcus bromii* has been shown to be pivotal in initiating breakdown of resistant starch in vitro (Ze et al 2012) even under conditions where it cannot grow (i.e. enzymes released from this bacteria start the initial resistant starch degradation process). Our data confirmed it is one of the predominant *Ruminococcus* species present in both MID and ELD age groups at baseline supporting *Bifidobacterium*-initiated degradation of resistant starch and then utilizing the fermentation endproducts from *Bifidobacterium* to produce butyrate.

In summary, this study is the first to demonstrate that MSPrebiotic® at 30 g/day is well tolerated and fits the criteria of being a prebiotic as it significantly increased the abundance of *Bifidobacterium* in mid-age and elderly Canadian adults. Furthermore, it produced a small but significant increase in relative abundance of butyrate in the elderly as well as a significant reduction in the use of stool softeners. In the elderly at baseline, there was significantly higher abundance of Proteobacteria (particularly Enterobacteriaceae, specifically the *E. coli/Shigella* group), which are considered to be pro-inflammatory, compared to mid-age adults but this difference was not detected after 12 weeks of consuming MSPrebiotic®. This demonstrates that MSPrebiotic® does modulate the gut microbiome and acts as a nutritional supplement that benefits the gut health of at least elderly and mid-age adults.

The Glucose reduction for the elderly group was found in both the DSM testing as well as the LipoScience analysis, supporting the validity of this finding. In addition, the insulin reduction for the elderly group found in the Lipo-Science analysis supports the value of MSPrebiotic® in lowering these parameters.

The reduction in the need for stool softeners in the elderly is important as the institutionalized population have many issues with bowel movement frequency and there is an individual and societal cost associated with the need for stool softeners. The increase in SCFAs in the elderly individuals taking MSPrebiotic® is indicative that this prebiotic improves the level of butyrate in the colon which in turn will lead to less autophagia of the gut colonocytes.

Of interest, there was increased butyrate in the elderly but not in the younger population stool samples despite both populations showing increased levels of *Bifidobacterium*.

There was also a significant decrease between week 0 and week 14 in the Glucose and Insulin level in the elderly group taking MSPrebiotic® compared to the elderly taking the Amioca control (Non-parametric p=0.0321 for Glucose reduction and p=0.0091 for Insulin reduction).

Specifically, the insulin level in the treatment group was reduced from approximately 15 µIU/ml to approximately 9 µIU/ml. In contrast, the control group stayed relatively constant, around 9-10 µIU/ml over the 14 week period.

As shown in FIG. 4, the glucose level in the treatment group decreased from approximately 106 mg/dL to approximately 100 mg/dL while the control group stayed relatively constant over the 14 week period, at around 106 mg/dL.

Furthermore, in the Elderly population, there was a steady decrease in serum glucose levels, from approximately 5.7 mmol/L to 5.2 mmol/L while serum glucose levels stayed relatively constant in the control group, at approximately 5.6 mmol/L.

It is important to note that for both the glucose levels and the serum glucose levels, the control and treatment groups were approximately identical at the start of the trial; however, while the control levels remained constant, the levels in the treatment groups decreased significantly.

This is consistent with previous research which showed that administration of MSPrebiotic® reduced blood sugar and decreased blood insulin levels and/or insulin resistance in an animal model.

Furthermore, while a number of studies have shown that obesity and metabolic disorders are associated with profound changes in gut microbiota, it has been shown that all three SCFAs protected against diet-induced obesity (Lin, 2012).

As such, this data confirms that MSPrebiotic® is an effective treatment for individuals with elevated blood glucose levels and/or insulin resistance.

As will be appreciated by one of skill in the art, there are several factors which can influence the structure and/or content of the gut microbiota, including, but by no means limited to, the host diet, infections and use of antibiotics (Petersen, 2014).

In general, it is considered that there are 3 types of dysbiosis: loss of beneficial microbial organisms; expansion of potentially harmful micro-organisms within the gut; and loss of overall microbial diversity. Specifically, it is theorized that reductions in beneficial bacteria and/or loss of microbial diversity can result in outgrowth of potentially pathogenic bacteria present in the gut microbiota. Alternatively, it is possible that outgrowth of potentially pathogenic bacteria results in reductions in levels of beneficial bacteria and/or loss of microbial diversity.

As discussed herein, the administration of an effective amount of resistant starch, for example, resistant potato starch, for example, an unmodified RS type 2 starch that is a *Solanum Tuberosum* Extract preparation, for example, MSPrebiotic®, on a dosage regime, has several benefits on the gut microbiome of an individual in need of such treatment, for example, by promoting a return to or promoting a normal gut microbiome or a return to a normal or non-dysbiotic gut microbiome.

As discussed herein, the dosage regimen may be an effective amount comprising 0.25-40 g of an unmodified RS type 2 potato starch administered to an individual as defined herein on a dosage regimen of daily for at least 12 weeks.

For example, the individual may be an individual who has gut microbiome dysbiosis. As discussed herein, the gut microbiome is highly complex and appears to be somewhat influenced by the diet of the individual; as such, determining what exactly constitutes a "healthy" or "normal" microbiome compared to one that is dysbiotic is not necessarily easy to determine. Furthermore, through senescence and changes in diet, the microbiome of an individual changes as that individual ages, typically becoming less diverse, as discussed herein. For example, as discussed above, the general composition of the gut microbiome has been reported to change with aging whereby there is a decrease in Actinobacteria and Bacteroidetes and an increase in Firmicutes. However, in addition to these ratios being dependent on the diet of the individual, it is further complicated by the fact that all individuals do not experience senescence or "age" at the same rate. Accordingly, for a given individual suffering from or having a dysbiotic gut microbiome, returning to or promoting a "normal gut microbiome" or "more normal gut microbiome" or "symbiotic gut microbiome" or "more symbiotic gut microbiome" may refer to the gut microbiome composition or profile of a healthy individual of similar age who consumes a similar diet or may refer to the gut microbiome profile or composition that the said individual had when younger. Alternatively, a normal gut microbiome for the said individual may refer to a gut microbiome in which the levels of Actinobacteria and/or Bacteroidetes have increased. The improvement in the ratio of beneficial bacteria to pathogenic bacteria in turn results in beneficial health effect for the individual, as discussed herein. In yet other embodiments, the individual is an individual who is at least 65 years of age or at least 70 years of age as discussed herein.

Accordingly, in some embodiments, there is provided a method of determining if an individual should be administered MSPrebiotic® or another suitable resistant potato starch on a dosage regimen, comprising: measuring the populations of Firmicutes and/or Bacteriodetes in the gut microbiome of the individual; measuring the populations of Firmicutes and/or Bacteriodetes in the gut microbiome of a control individual consuming a similar diet; comparing the populations; and determining if said individual has a dysbiotic microbiome. Specifically, if the Firmicutes and/or Bacteriodetes population in the gut microbiome of the individual differs for example differs significantly from the Firmicutes and/or Bacteriodetes population in the gut microbiome of the control individual, either in for example percentage of the gut microbiome, the individual is dysbiotic.

In another aspect of the invention, there is provided a method of promoting a symbiotic gut microbiome or a more beneficial gut microbiome or a more beneficial gut microbiome profile in an individual in need of such treatment comprising administering to said individual MSPrebiotic® or another suitable resistant potato starch on a dosage regimen.

For example, the individual may be an individual who has or who is suspected of having or is at risk of developing a dysbiotic gut microbiome. Such individuals include but are by no means limited to: individuals who have been administered antibiotics; individuals who have been or are being hospitalized or have entered a long term care facility or are otherwise being subjected to a more restrictive or less varied diet than before or previously; individuals suffering from or thought to be suffering from diseases in which gut microbiome dysbiosis has been implicated, for example but by no means limited to irritable bowel syndrome, inflammatory bowel disease, Crohn's disease, ulcerative colitis and the like; an individual who has abnormally high levels of a member of the family Enterobacteriaceae for example phylum Proteobacteria or who may have been exposed to or otherwise infected with a member of the family Enterobacteriaceae for example phylum Proteobacteria; and an elderly individual for example an individual of 65 years or older or of 70 years or older. In some preferred embodiments, the individual is an elderly individual of 65 years or older or of 70 years or older.

It is of note that individuals who have gut microbiome dysbiosis can also be determined using analyses such as those described herein for determining relative levels of bacteria within the gut microbiome, for example, by determining diversity thereof or by determining levels of specific bacteria of interest, for example, at the family, genera or species level.

Accordingly, in some embodiments, there is provided a method of determining if an individual should be administered MSPrebiotic® or another suitable resistant potato starch on a dosage regimen, comprising: determining relative levels of bacteria within the gut microbiome, for example, by determining diversity thereof or by determining levels of specific bacteria of interest of the individual; determining relative levels of bacteria within the gut microbiome, for example, by determining diversity thereof or by determining levels of specific bacteria of interest of a healthy control individual consuming a similar diet; comparing the populations; and determining if said individual has a dysbiotic microbiome. Specifically, if the gut microbiome diversity or levels of specific bacteria in the gut microbiome of the individual differs for example differs significantly from the diversity of the gut microbiome or levels of specific bacteria in the gut microbiome of the control individual, the individual is dysbiotic.

As discussed herein, promotion of a non-dysbiotic or symbiotic gut microbiome is accomplished by promoting an increase in the abundance of *Bifidobacterium* as a result of administration of MSPrebiotic®. As discussed above, while the percentage of *B. dentium* decreased with MSPrebiotic® consumption, the percentage of *B. pseudocatenulatum* and/or *B. ruminantium* increased in the cohort taking MSPrebiotic®. Along with Lactobacilli, Bifidobacteria are associated with good gut health.

For example, *Bifidobacterium pseudocatenulatum* has been shown to reduce obesity-associated inflammation by restoring the lymphocyte-macrophage balance and gut microbiota structure in high-fat diet-fed mice. (Moya-Perez, 2015)

Furthermore, *Bifidobacterium pseudocatenulatum* are capable of degrading phytate/phytic acid, which normally bind and precipitates divalent cations like Ca and Zn, which limits their absorption. Thus, absorption of these minerals can be increased in the presence of *B. pseudocatenulatum*, as discussed herein.

Furthermore, *B. pseudocatenulatum* promotes conjugated linoleic acid synthesis, which is a component touted as promoting health and fighting cancer.

*B. pseudocatenulatum* also reduces inflammation by increasing IL-10, which acts on Treg cells to 'sharpen' the immune system, and reducing inflammatory substance secretion.

*B. pseudocatenulatum* reduced cholesterol, blood glucose levels, and weight in animal models.

*B. pseudocatenulatum* promotes folate synthesis in the gut.

*B. pseudocatenulatum* inhibits pathogenic bacteria growth of both *E. coli* and *Salmonella* bacteria.

Bifidobacteria may also provide protection of DNA from induced damage by carcinogens, reduce incidences of diarrhea, maintain remission from inflammatory bowel disease and promote colon regularity (O'Callaghan 2016).

The fact that levels of *B. dentium* were decreased is also significant, as this bacteria is human-specific bacteria that is frequently found in dental caries, saliva, and feces and is frequently referred to as an opportunistic pathogen, ie. bad bacteria.

Other strains of Bifidobacteria are known to have beneficial effects on humans.

For example, *B. adolescentis* is an important intermediate producer in cross-feeding of Firmicutes bacteria for butyrate production. *B. adolescentis* prevents NSAID-induced ulcers and has anti-inflammatory effects. Like *B. pseudocatenulatum*, *B. adolescentis* degrades phytic acid, enhances folate production and inhibits the growth of pathogenic bacteria. *B. adolescentis* has also been shown to have anti-viral properties against viruses such as the Coxsackie Virus, Norovirus, Hepatitis B, and some retroviruses. Finally, *B. adolesentis* produces GABA.

Furthermore, *Bifidobacterium breve* interacts with dendritic cells and regulatory T cells, to reduce inflammation. This reduces the risk of allergy development and promotes antibody responses to legitimate threats, such as viruses and pathogenic bacteria. *B. breve* also plays a role in suppressing colitis flare-ups but not in the prevention of symptoms. *B. breve* is an efficient converter of linoleic acid to conjugated linoleic acid, which is implicated in cancer prevention and affects chloride secretion in the gut, which influences water absorption.

Yet further, *Bifidobacterium longum* has been shown to have anti-inflammatory effects related to activities on regulatory T cells. Furthermore, *B. longum* has a positive effect on celiac patients and affects the antigenicity of gliadin, the protein in gluten that triggers celiac disease. *B. longum* also has positive effects on tumor formation and progression in animal models. *B. longum* also inhibits the growth of various opportunistic pathogenic gut bacteria and *B. longum* supplementation has positive effects on colitis and Crohn's disease symptoms in animal models and humans. *B. longum* appears to help reduce allergic responses to pollen and food allergens and to reduce susceptibility to influenza and rotavirus viruses. *B. longum* also positively affects bone health and mineral absorption and promotes relief from constipation and diarrhea.

During adult life, the Bifidobacteria population stabilizes to represent 3-6% of the total gut microbial population, whereas in elderly (>65 years) the bifidobacterial numbers usually decline with age (Hopkins, 2001; Satokari, 2003).

Furthermore, it is important to note that this increase occurred in both the mid-age and elderly populations, indicating that resistant potato starch, for example, MSPrebiotic®, will promote good gut health by increasing the Bifidobacteria levels present in the gut microbiome of an individual in need of such treatment, for example, an individual who is suffering from poor gut health, low levels of Bifidobacteria within the gut microbiome, for example, below, 6% of the total gut microbial population, below 5%, below 4% or below 3%, and/or low levels of butyrate, as discussed herein. Specifically, it is known that as we age, the numbers of *Bifidobacterium* found lining the large intestinal wall naturally begins to decline. As demonstrated herein, this in turn results in a reduction in butyrate levels which in turn impacts colon health.

Specifically, the presence of the resistant potato starch provided the Bifidobacteria with a preferred growth source or food source which in turn resulted in the Bifidobacteria out-growing and/or out-competing other, potentially less-beneficial, bacteria within the gut microbiome.

Accordingly, the present invention provides a method for maintaining and/or restoring the intestinal flora or gut microbiome or for altering the gut bacterial population or gut microbiome towards a healthier composition or profile or less dysbiotic profile by stimulating the growth of Bifidobacteria such as for example but by no means limited to *B. adolescentis, B. pseudocatenulatum* and *B. ruminantium*. It is of note that as discussed herein, this occurs without added probiotics such as supplementing the prebiotic with a supply of *B. adolescentis, B. pseudocatenulatum* and/or *B. ruminantium*. Accordingly, in some embodiments, this increase in *Bifidobacterium* levels occurs with the proviso that no probiotic is added. However, in other embodiments, the resistant potato starch may be coadministered or administered simultaneously with suitable *Bifidobacterium* such as for example *B. adolescentis, B. pseudocatenulatum* and/or *B. ruminantium*.

Accordingly, in some embodiments, there is provided a method of determining if an individual should be administered MSPrebiotic® or another suitable resistant potato starch on a dosage regimen, comprising: measuring the populations of *Bifidobacterium* in the gut microbiome of the individual; measuring the populations of *Bifidobacterium* in the gut microbiome of a healthy control individual consuming a similar diet; comparing the populations; and determining if said individual has low levels of *Bifidobacterium* in their gut microbiome.

For example, an individual who is in need of such treatment may be an individual whose gut microbiota has less than 5%, less than 4% or less than 3% bifidobacterial content.

Accordingly, in some embodiments, there is provided a method of increasing Bifidobacteria content in the gut microbiota of an individual in need of such treatment comprising administering to said individual MSPrebiotic® or another suitable resistant potato starch on a dosage regimen.

Furthermore, it is noted that *Bifidobacterium* strains have been demonstrated to have properties that would be specifically beneficial to human infants and young children.

For example, *B. longum* has been shown to provide protection against rotavirus infection, alleviation of food allergies, and prevent diarrhea and constipation. *B. pseudocatenulatum* modulates the consequences of chronic stress on the HPA response produced by maternal separation during infancy. *B. breve* inhibited, dose dependently, Caco-2 cell invasion by enteropathogenic *E. coli, Yersinia pseudotuberculosis*, and *S. typhimurium* strains. *Bifidobacterium breve* has also been shown to be effective in increasing stool frequency in children with functional constipation. *B. breve* mediates anti-inflammatory and antiallergic reactions by modulating the expression of inflammatory molecules during the newborn period and by regulating the expression of co-stimulatory molecules during the weaning period. *B. adolescentis* is associated with the saliva of young patients who have never had periodontal disease. *B. adolescentis* also decreased the growth of *S. mutans*, which is a risk factor for dental caries.

As such, in some embodiments, there individual in need of such treatment may be a human infant who would benefit from increased levels of *Bifidobacterium*, as discussed above.

In other embodiments, the prebiotic may be coadministered or administered simultaneously with an effective amount of a suitable probiotic, for example, but by no means limited to: *L. acidophilus; L. fermentum; L. plantarum; L. rhamnosus; L. salivarius; L. paracasei; L. reuteri; B. bifidum; B. adolescentis; B. longum; B. pseudocatenulatum*; and/or *B. ruminantium*. It is of note that in these embodiments, MSPsynbiotic®, an unmodified RS type 2 starch that is a *Solanum Tuberosum* Extract preparation of food grade quality for animal and human food application but designed specifically for use in combination with probiotics or other prebiotics may be used.

Furthermore, as discussed herein, resistant potato starch, specifically, MSPrebiotic®, has been demonstrated to increase the production of butyrate in elderly individuals.

Furthermore, particular Bifidobacteria that are elevated in subjects taking MSPrebiotic® secrete phytases, which degrade phytic acid. Phytic acid has a strong binding affinity to important minerals such as calcium, iron, and zinc. Accordingly, as a result of increased degradation of phytic acid, absorption of these minerals will be increased in these individuals. As will be apparent to one of skill in the art, enhanced or increased absorption of calcium is important in the elderly, many of whom suffer from osteoporosis. Furthermore, increased iron absorption is associated with increased red blood cell and hemoglobin counts. Zinc is required for host immune system function and also plays a role in cell division, cell growth, wound healing, and the breakdown of carbohydrates.

Furthermore, short chain fatty acid production in the gastro-intestinal tract has been demonstrated to lower pH, improve availability of calcium and magnesium and inhibit potentially pathogenic bacteria (O'Callaghan, 2016).

While not wishing to be bound to a particular theory or hypothesis, the inventors note that in the mid-age test population, Bifidobacteria levels are increased compared to the elderly population. This suggests that while more butyrate is produced as a result of the fermentation of MSPrebiotic® by the members of this group, but the mid-age test population likely have enough healthy colon cells that feed on the butyrate produced by Bifidobacteria so that no excess butyrate is detected.

However, with the elderly population, Bifidobacteria levels go up, and the Bifidobacteria cross feed the Firmicutes who produce more butyrate. The butyrate produced is more than the colon cells that exist can utilize. It is believed that the butyrate level goes down over time as more healthy colon cells are produced and accordingly more butyrate is consumed.

Accordingly, administration of MSPrebiotic® on a dosage regime can be used to increase butyrate levels in any individual in need of increased butyrate levels, for example, an individual who is older than 70 years of age or 65 years of age or 60 years of age or an individual who is at risk of developing or who has poor colon health or who has or is suspected of having reduced butyrate levels.

According to an aspect of the invention, there is provided a method for increasing butyrate levels within the colon of an elderly individual comprising administering to said individual an effective amount of MSPrebiotic® or another suitable resistant potato starch on a dosage regime.

For example, the butyrate levels may be compared to an individual of similar age and condition fed a similar diet excluding an effective amount of resistant potato starch (a control diet) or may compared to a standard or threshold level known in the art.

Furthermore, administration of MSPrebiotic® on a dosage regime has been demonstrated to reduce levels of members of the family Enterobacteriaceae for example the phylum Proteobacteria such as for example *Escherichia* and *Shigella* bacteria, both of which are known to produce Shiga toxin and are associated with a number of human diseases. Accordingly, an individual suffering from a disease associated with Shiga toxin and/or with abnormally high levels or undesirably high levels of *Escherichia* and/or *Shigella* can be treated by administration of MSPrebiotic® on a dosage regime.

Accordingly, in some embodiments, there is provided a method of reducing Enterobacteriaceae and/or Proteobacteria content in the gut microbiota of an individual in need of such treatment comprising administering to said individual MSPrebiotic® or another suitable resistant potato starch on a dosage regimen.

An individual in need of such treatment may be an individual infected with or suspected of being infected with Shiga toxin-producing *E. coli* (STEC). Most people infected with STEC develop diarrhea (often bloody) and abdominal cramps. As such, administration of an effective amount of resistant potato starch to such an individual on a suitable dosage regimen will result in a reduction in the severity of or frequency of abdominal cramps and/or diarrhea.

In general, *E. coli* is a frequent cause of hospital-acquired infections, so reducing levels in institutionalized populations by administering an effective amount of resistant potato starch as discussed herein is an attractive proactive measure for reducing infections. For example, GI-derived *E. coli* is the most common cause of urinary tract infections (UTI), so reducing *E. coli* in stools will reduce the risk of an individual acquiring a UTI.

In addition to causing diarrhea, the toxins produced by *E. coli* can cause increased intestinal permeability, which can lead to various negative consequences.

As discussed above, in a healthy gut, pathogens such as *Escherichia* and *Shigella* are typically kept at low levels. However, outgrowth of these organisms can contribute to disease. For example, *E. coli* has been shown to be sufficient to cause colitis in some cases. Furthermore, the expansion of Enterobacteriaceae is also seen in patients suffering from Crohn's disease and ulcerative colitis in both tissue and fecal samples (Petersen, 2014). *E. coli* has been associated with symptomatic irritable bowel syndrome (IBS).

While not wishing to be bound to a particular theory or hypothesis, it is believed that the resistant potato starch serves as a poor growth medium or food source for strains of *Escherichia* and/or *Shigella* and/or serves as a good growth medium or food source for other bacteria present in the gut microbiome which are then able to out-compete the *Escherichia* and/or *Shigella* strains, thereby resulting in a reduction in their levels within the gut microbiome or gut flora. Accordingly, administration of MSPrebiotic® on a dosage regime may be used in place of or in combination with other treatments for *Escherichia* and/or *Shigella*, such as for example, targeted antibiotic treatments or antibody treatments.

In other embodiments, the resistant potato starch may be co-administered with a suitable probiotic or prebiotic which will promote growth of beneficial bacteria to out-compete or otherwise reduce the levels of the pathogenic bacteria. One suitable probiotic would be one of the various beneficial strains of Bifidobacteria, as discussed herein. Other suitable co-supplements will be readily apparent to one of skill in the art.

Furthermore, the effective amount may vary according to many different factors, for example, the age, weight, and/or condition of the individual. It is of note that the appropriate effective amount for a given individual can be easily determined through routine experimentation.

For illustrative purposes, an "effective amount", particularly for humans, may be 0.25 grams to 40 grams of MSPrebiotic® Resistant Potato Starch. Alternatively, an effective amount may be 0.5 grams to 40 grams or 0.25 grams to 30 grams or 0.5 grams to 30 grams, or 1.0 grams to 40 grams, or 1.0 grams to 30 grams, or 5.0 grams to 30 grams, or 5.0 to 40 grams, or 10.0 grams to 30 grams or 10.0 grams to 40 grams.

Accordingly, in some embodiments, a "dosage regimen" comprises administration of 0.25 grams to 40 grams of MSPrebiotic® Resistant Potato Starch or another suitable resistant potato starch daily for a period of time. That is, in some embodiments, the dosage regimen is daily administration of an effective amount of MSPrebiotic® Resistant Potato Starch or another suitable resistant potato starch.

As will be appreciated by one of skill in the art, "daily" does not necessarily mean every day but can refer to for example 6 out of 7 days, 3 out of 4 days, every other day or the like. Of course, following a daily regimen will result in better results but beneficial results are obtained even when MSPrebiotic® Resistant Potato Starch or suitable resistant potato starch is not administered every day.

As will be appreciated by one of skill in the art, a suitable period of time will of course depend on the reason for the administration of MSPrebiotic® Resistant Potato Starch or other suitable resistant potato starch as well as the age, general condition and/or severity of gut microbiome dysbiosis of the individual. For example, the suitable period of time may be from one week, two weeks, a few weeks, one month, two months, a few months, 12 weeks or several months, after which time the individual may take a lower maintenance daily dose or may be administered a regular dose less frequently, for example, 3 or 4 times a week. Alternatively, the individual, who may be a human, may follow the dosage regimen indefinitely.

As will be appreciated by one of skill in the art, the "effective amount" may be taken on a regular schedule or regimen, for example, once per day or every other day.

It is important to note that the "effective amount" does not need to be taken in a single dose and may be taken in multiple or partial doses throughout the day, as discussed herein.

For example, convenient dosages of resistant starch include but are by no means limited to for example 250 mg capsules or tablets, 500 mg capsules or tablets, a teaspoon of resistant starch, a tablespoon of resistant starch and the like. As will be known by those of skill in the art, a "teaspoon" is typically considered to correspond to approximately 3.5 grams while a tablespoon is considered to correspond to approximately 10 grams. The resistant starch may be in the form of a powder. Other suitable dosages will be readily apparent to one of skill in the art.

It is noted that in some embodiments, the "effective amount" may be for example one or more teaspoon(s) of MSPrebiotic® Resistant Potato Starch, for example, one, two, three or four teaspoon(s) MSPrebiotic® Resistant Potato Starch. In some embodiments, this dosage may be taken on a regular schedule or regime, for example, once per day, twice per day, three times per day, four times per day, every other day or as needed or desired.

In yet other embodiments, the "effective amount" may be for example one or more tablespoon(s) of MSPrebiotic® Resistant Potato Starch, for example, one, two or three tablespoon(s) MSPrebiotic® Resistant Potato Starch. In some embodiments, this dosage may be taken on a regular schedule or regime, for example, once per day, twice per day, three times per day, four times per day, every other day or as needed or desired.

As discussed herein, other forms of resistant starch may be used within the invention, provided the product or medicament comprising the resistant starch, for example resistant potato starch, for example MSPrebiotic® Resistant Potato Starch, is high in resistant starch. As used herein, a starch that has "high" resistant starch content is a starch that is at least 60% resistant starch.

Accordingly, in the embodiments discussed herein, the resistant potato starch used in the embodiments of the invention is at least 60% resistant starch or at least 65% resistant starch or at least 70% resistant starch or at least 75% resistant starch or at least 80% resistant starch.

Yet further, the inventors have discovered that a key aspect in maintaining the integrity of the resistant starch, specifically, maintaining the starch at a temperature below 60 C. As will be apparent to one of skill in the art, this includes production of the resistant starch itself and also preparation of medicaments such as tablets and capsules and functional foods and/or beverages to which the resistant starch is added.

As discussed herein, considerable care must be taken to ensure that as much of the resistant starch is retained as possible. As discussed below, the inventors have discovered that there are several additional considerations beyond maintaining a temperature below 60° C. when preparing pharmaceutical products such as tablets and capsules from resistant starch such as moisture content of the starch and pressure used in tablet formation.

As will be appreciated by one of skill in the art, the capsules and tablets may be made in any suitable size, for example, in a unit dosage to be taken once per day, or in dosages to be taken multiple times per day, for example twice or more per day on a suitable dosage regimen or schedule. For example, a suitable dosage regimen may be one or more capsules or tablets comprising 50-750 mg resistant starch prepared as discussed herein every 2, 4, 6, 8, 12 or 24 hours or taken with meals.

For example, the capsules or tablets may be 50 mg, 100 mg, 200 mg, 220 mg, 250 mg, 300 mg, 350 mg, 400 mg, 450 mg, 500 mg, 600 mg, 700 mg, 750 mg or any suitable similar size according to patient and/or consumer preference.

In some embodiments, each capsule may weigh 625±5.0 mg and each capsule may contain 528±17.6 mg of material of which 350-370 mg is resistant starch.

In some embodiments, the material is formed into tablets at a pressure between 45-100 MPa or between 60-100 MPa. In some embodiments, each tablet is 40-50% resistant starch, for example, 45% resistant starch.

In other embodiments, the "effective amount" may be a resistant starch capsule or tablet. The resistant starch capsule or tablet may be prepared according to the methods described herein. Preferably, the resistant starch capsule is a 500 mg capsule. The tablet may be a 220 mg tablet or a 250 mg tablet.

The invention will now be further explained and elucidated by way of examples; however, the invention is not necessarily limited by the examples.

Results:

There were 200 participants screened for eligibility, 112 of whom were enrolled and 84 who completed the study (42 elderly and 42 mid-aged). In the elderly age group (ELD) there were 11 residents of a long term care home and 31 participants residing in the community (randomization: 20 to Placebo and 22 to MSPrebiotic®), whereas all the mid-age group (MID) were adults residing in the community (randomization: 21 to placebo and 21 to MSPrebiotic®). There were 25/42 (59.5%) of ELD and 24/42 (57.1%) of MID participants who were women. The average age was 78.4±7.66 (range of 70 to 96) and 41.6±5.61 (range of 32 to 50) years for the ELD and MID cohorts, respectively.

The compliance with consuming the study product was: MID-Placebo; 93.5%, MID-MS Prebiotic®; 91.7%, ELD-Placebo; 95.4% and ELD-MSPrebiotic®; 97.2%. This data was from the daily log completed by all participants and the study co-ordinator documented if there was any returned study product at the five clinic visits where samples were collected (FIG. 1).

For the microbiome 16S sequencing analysis the mean number of reads per sample was 110,138±54,843.18. There were 6 MiSeq runs performed and the average error rate for these runs was 0.061% (Pool 1; 0.06022091%, Pool 2; 0.06193126%, Pool 3; 0.06213357%, Pool 4; 0.06133254%, Pool 5; 0.0601509%, Pool 6; 0.06123075%). The total 434,632 OTUs were filtered by phyloseq (McMurdie et al 2013) to remove all singletons and this filtered data (60,212 OTUs for baseline data and 56,589 OTUs for week 14 data) was used for the analysis. Data were excluded if participants took antibiotics during the course of the study within the 5 weeks before the stool sample was collected. The week 0 and week 14 sequencing data for one MID and one ELD participant both in the MSPrebiotic® cohort were removed due to antibiotic consumption. In addition the week 14 sequencing data for three ELD in the placebo and one ELD in the MSPrebiotic® cohorts were removed due to antibiotic consumption.

Figure 2A:
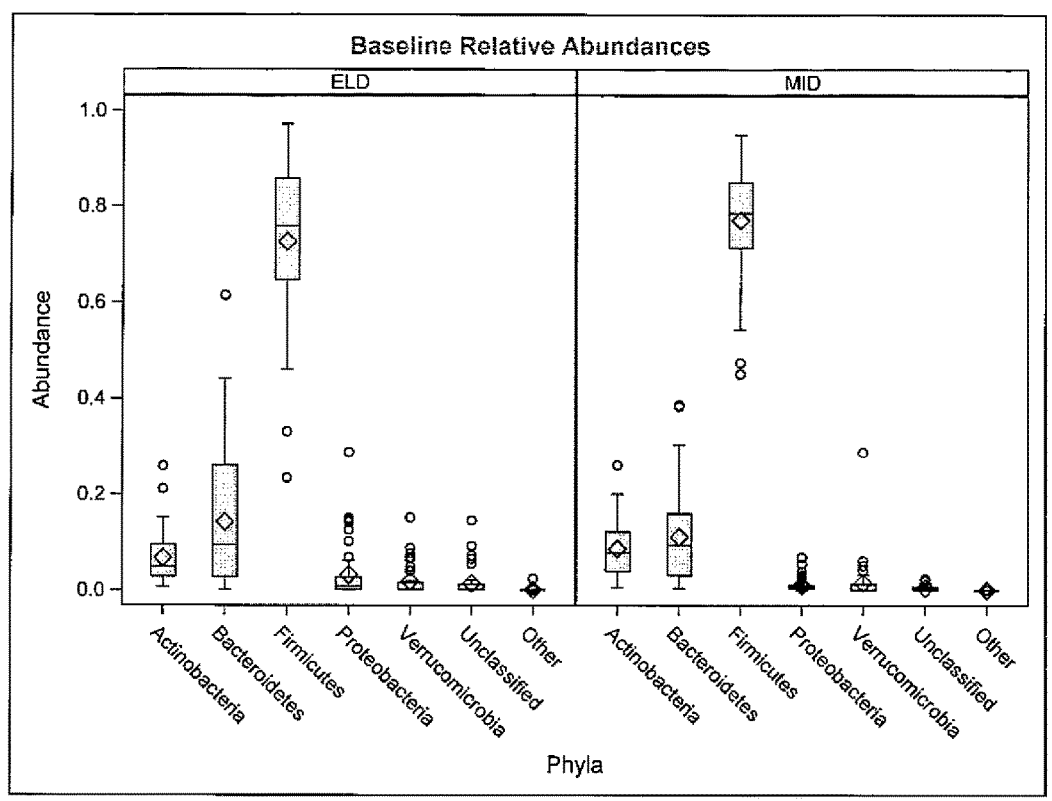
FIG. 2 Relative Abundance of phyla and genera for Elderly and Mid-age groups at baseline. The cohort mean is shown by the diamond symbol within the box, the median is shown as a cross-bar within the box and the vertical bars represent the standard error. Stool samples were analyzed from 42 participants in each of the elderly as well as the mid-age cohorts. The phylum results (A) for both ELD and MID, as well as the genus results for ELD (B) and MID cohorts (C) are shown for the baseline stool samples. Those phylum and genus with less than 0.01% were considered as rare and were grouped together as "Other".
Figure 2B:
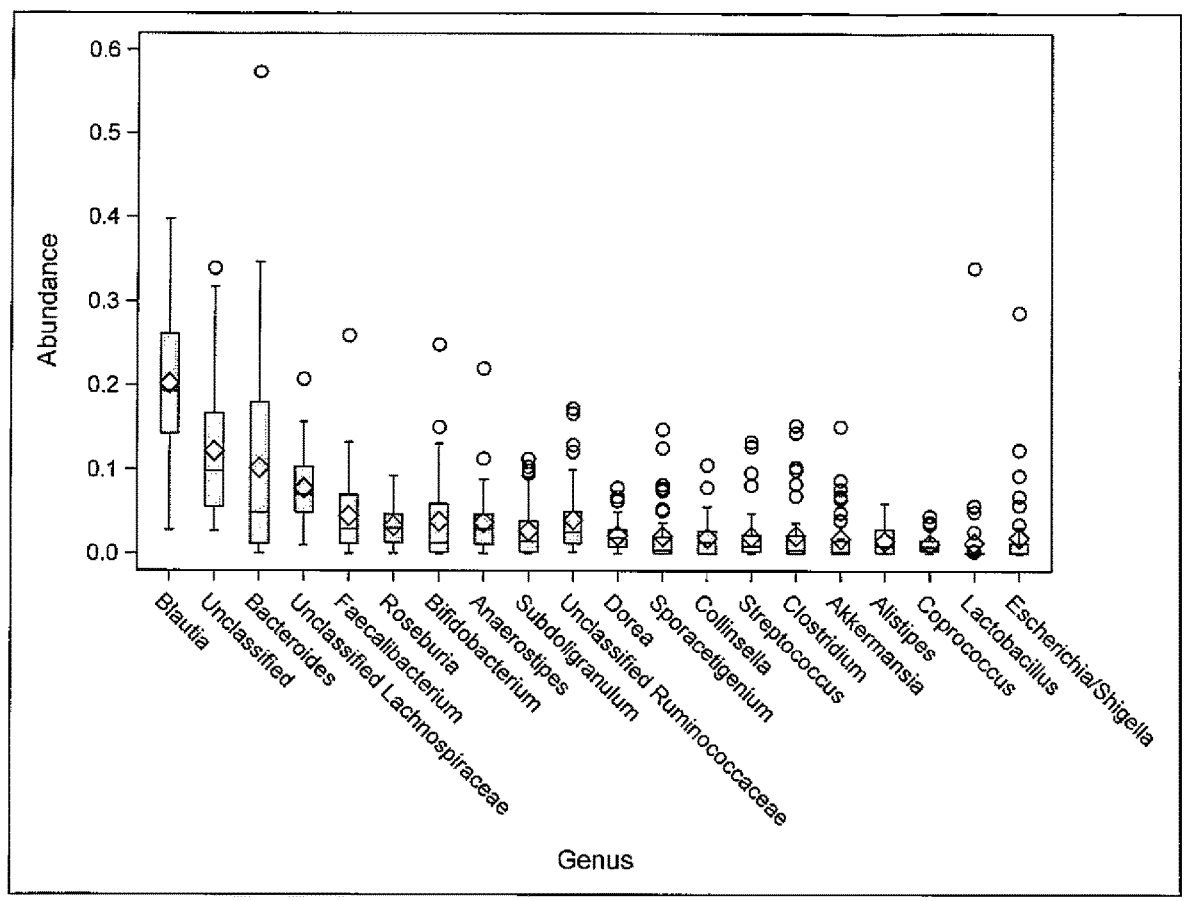
Figure 2C:
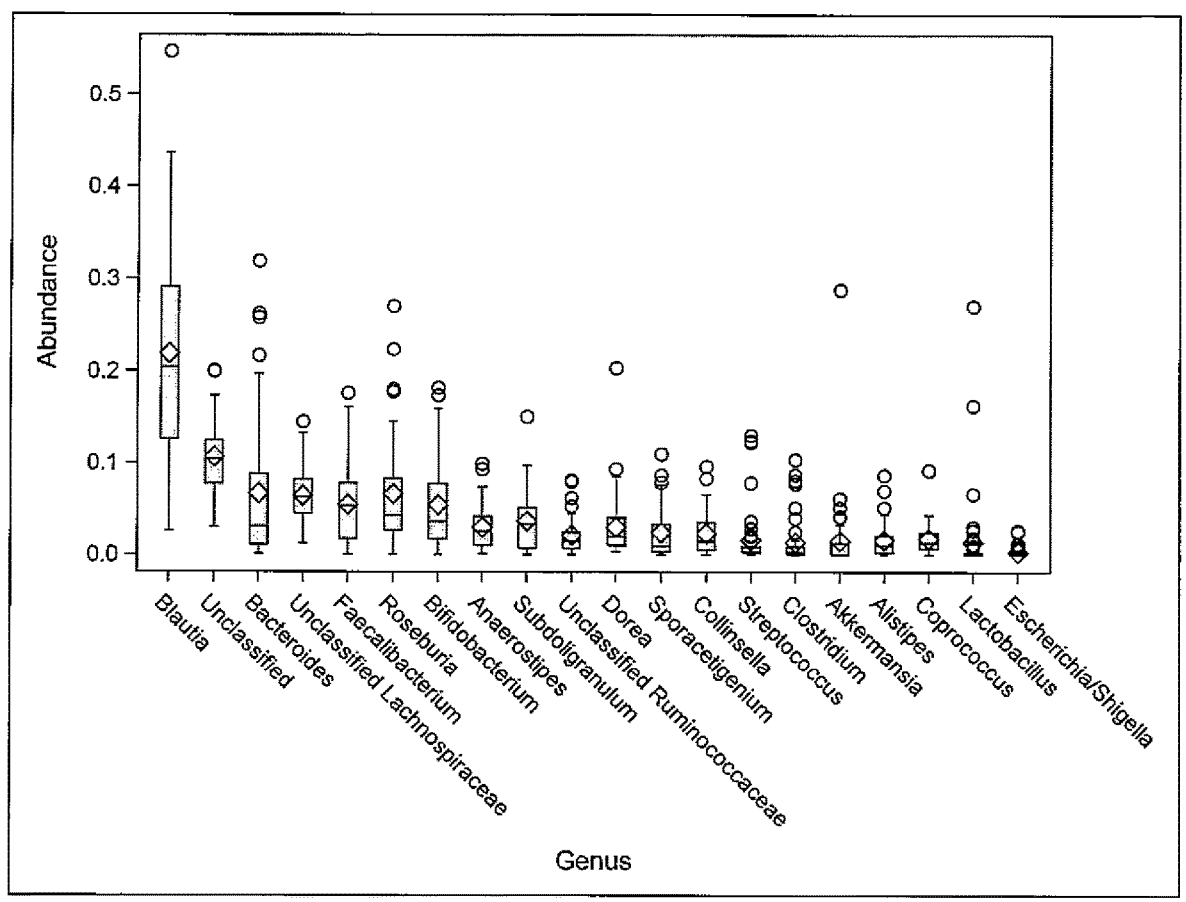

The relative abundance at baseline of the top five phyla and the top 20 genera are shown in FIG. 2. At baseline there were significant differences at the phyla level between ELD and MID participants (Table 1). Firmicutes, Proteobacteria and Verrucomicrobia were all significantly higher in the ELD compared to MID. The significant differences at the genus level at baseline are also shown in Table 1.

Figure 3A:
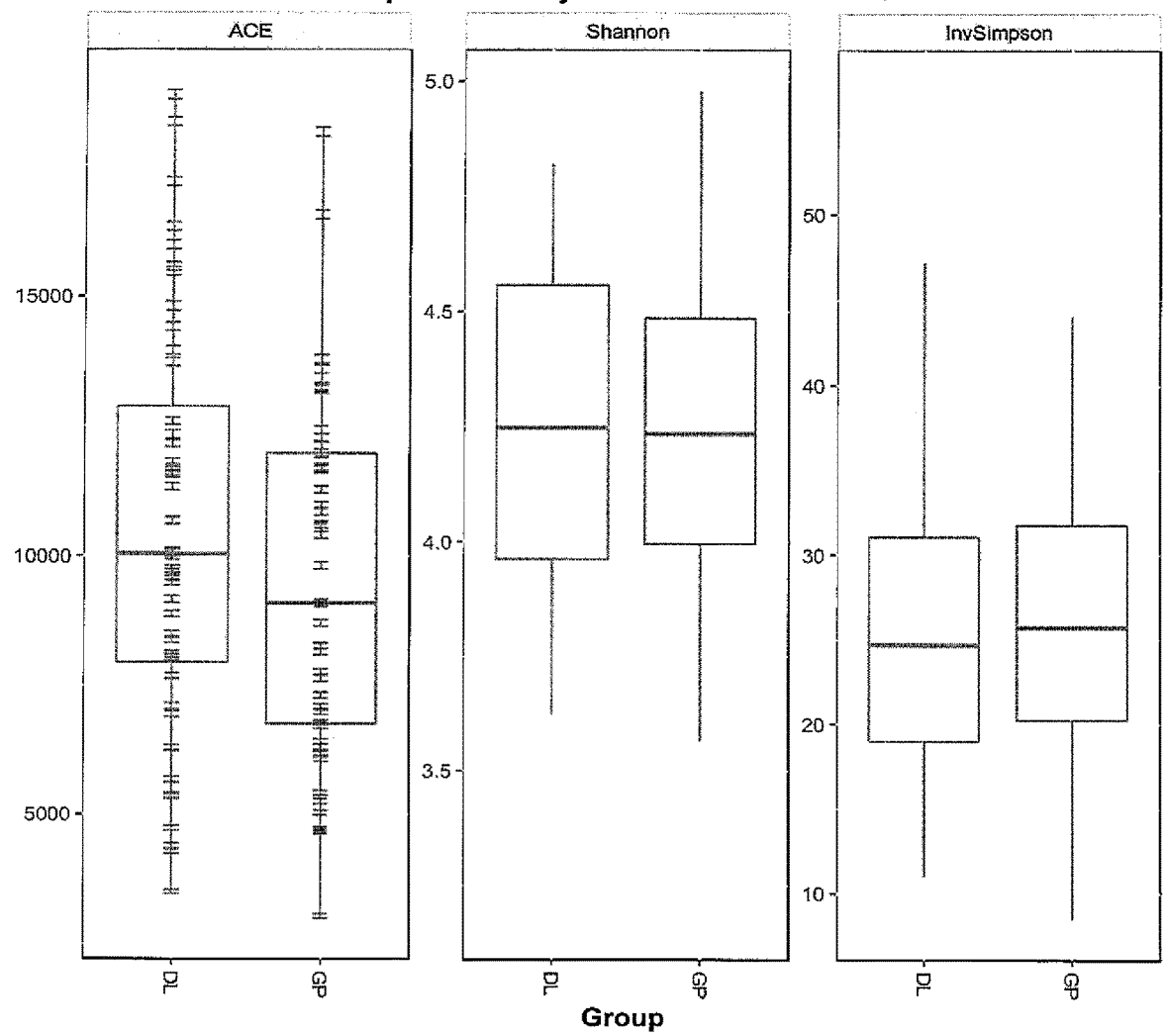
FIG. 3: Alpha diversity metrics for the microbiome of ELD and MID cohorts at baseline showed no significant differences (A). At week 14 (B) there were significant treatment differences for both ELD and MID cohorts on MSPrebiotic® compared to Placebo ($p_{adjusted}$=0.0131 for Shannon and $p_{adjusted}$=0.0036 for Inv Simpson). ACE is an assessment of "richness" (i.e. abundance of OTUs) whereas SHANNON and INV SIMPSON are assessments of both "richness" and "diversity" (i.e. different types of OTUs).
Figure 3B:
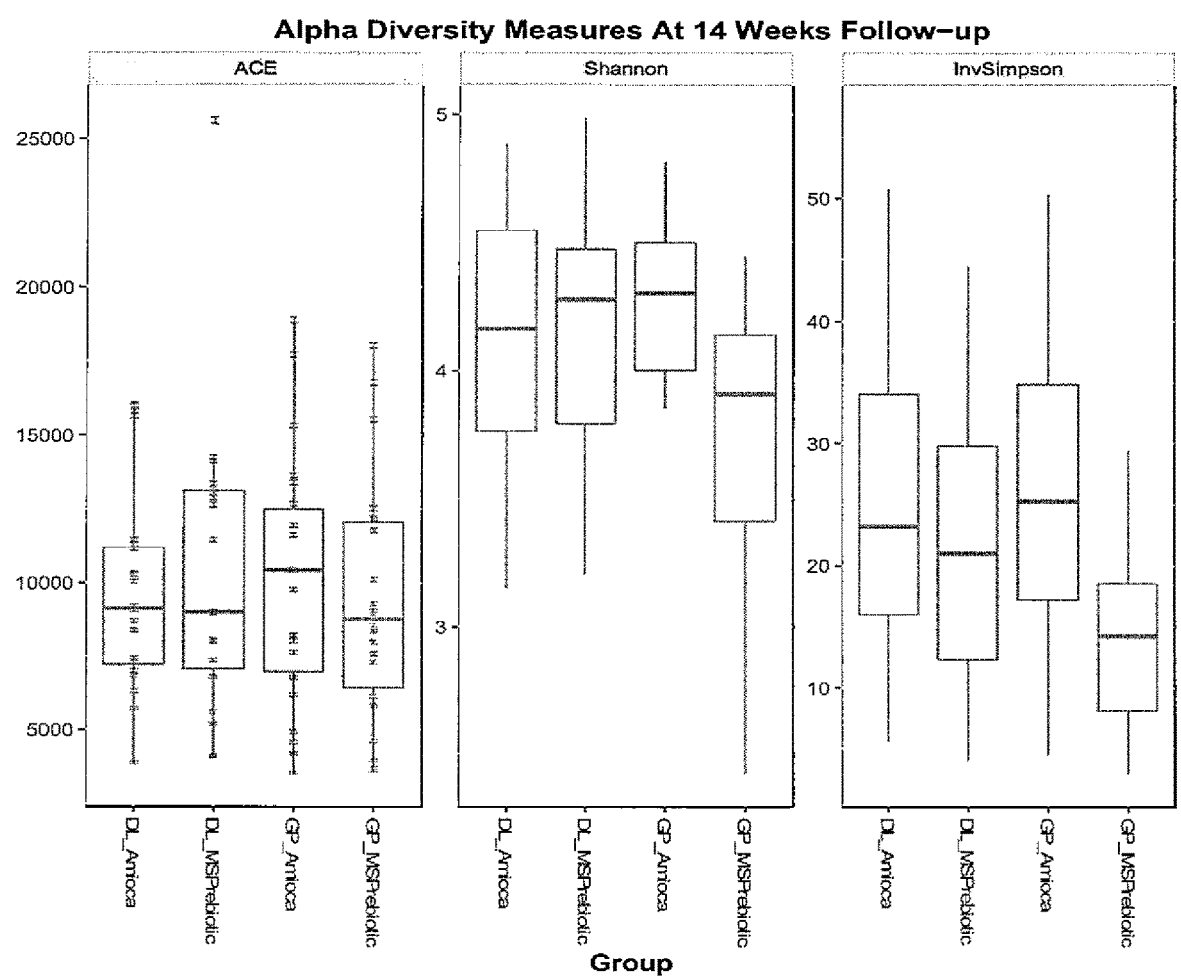
Figure 4A:
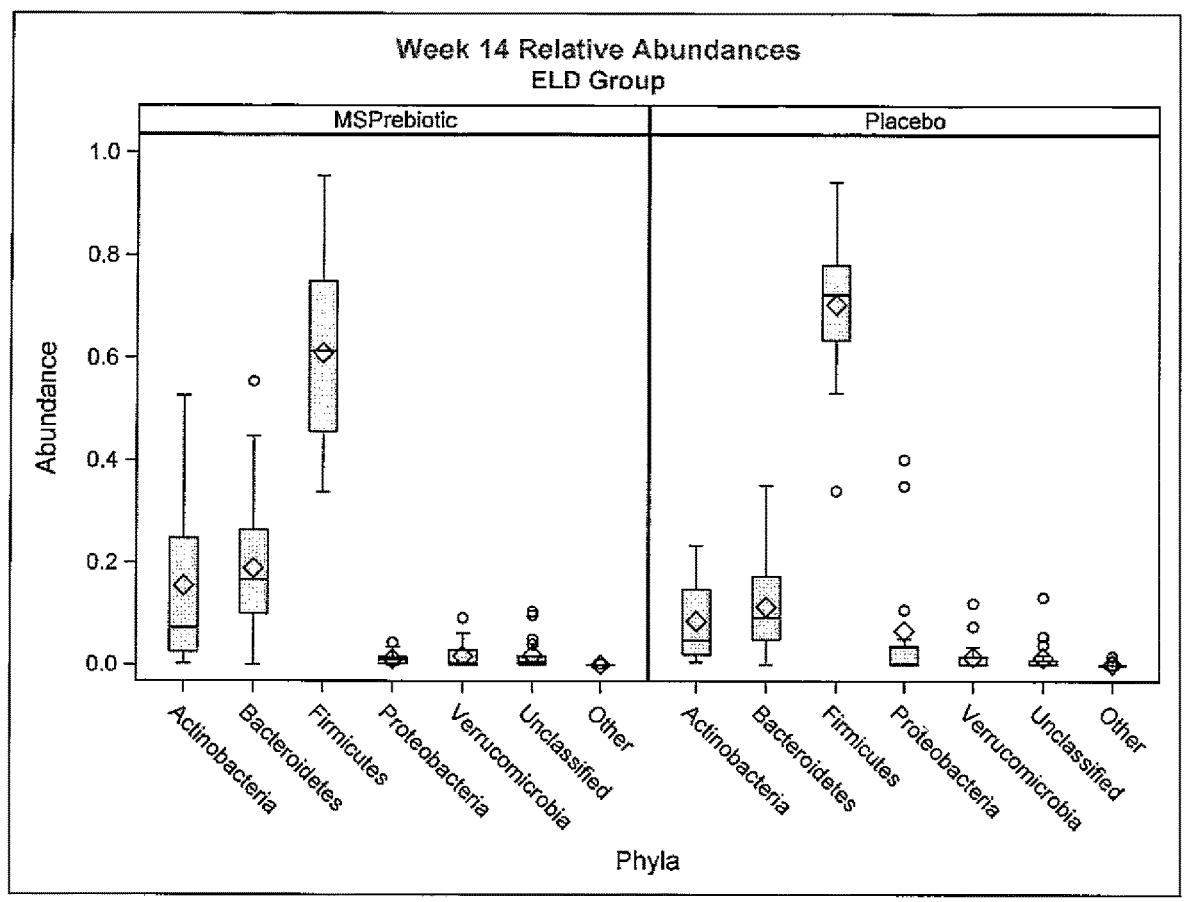
FIG. 4 Relative abundance of phylum and genera for elderly and mid-age groups after 12 weeks of consuming MSPrebiotic® or placebo. The relative phyla abundances for ELD (A) and the relative genera abundances are shown for ELD on Placebo (B) or MSPrebiotic® (C). The relative phylum abundances for MID (D) and the relative genera abundances are shown for MID on Placebo (E) or MSPrebiotic® (F). The cohort mean is shown by the diamond symbol within the box and the median is shown as a cross-bar within the box.
Figure 4B:
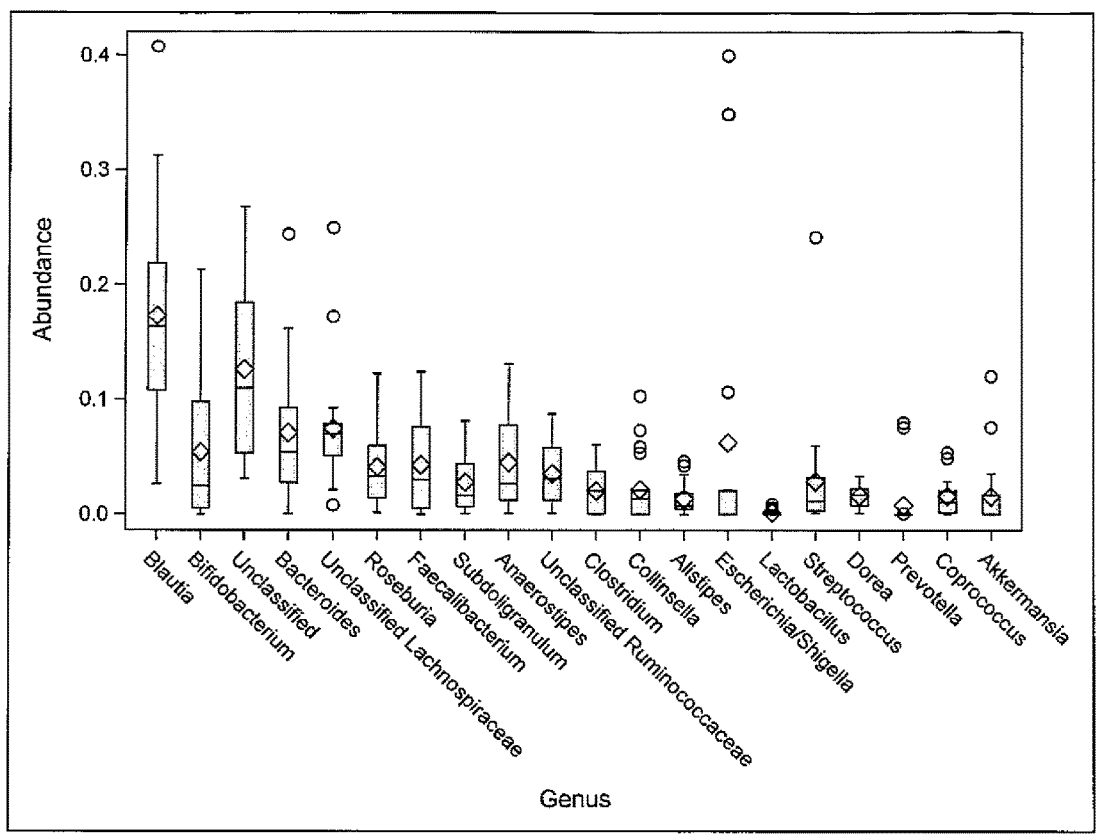
Figure 4C:
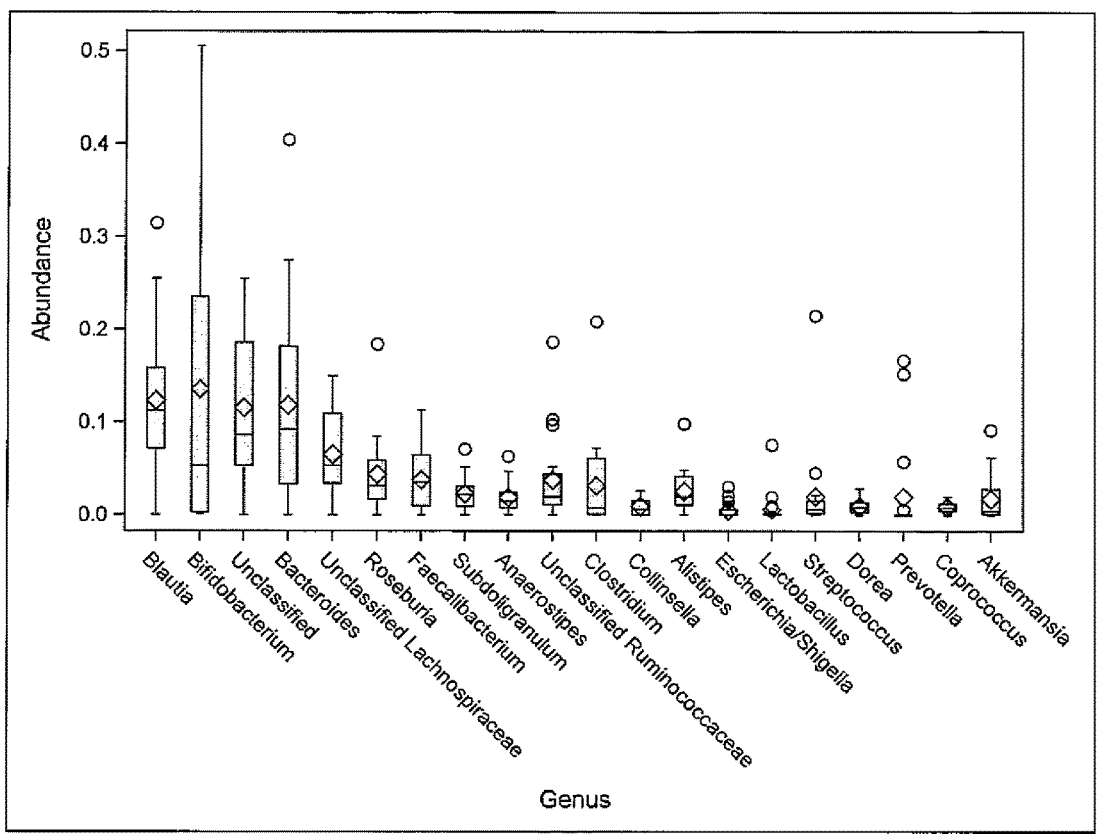
Figure 4D:
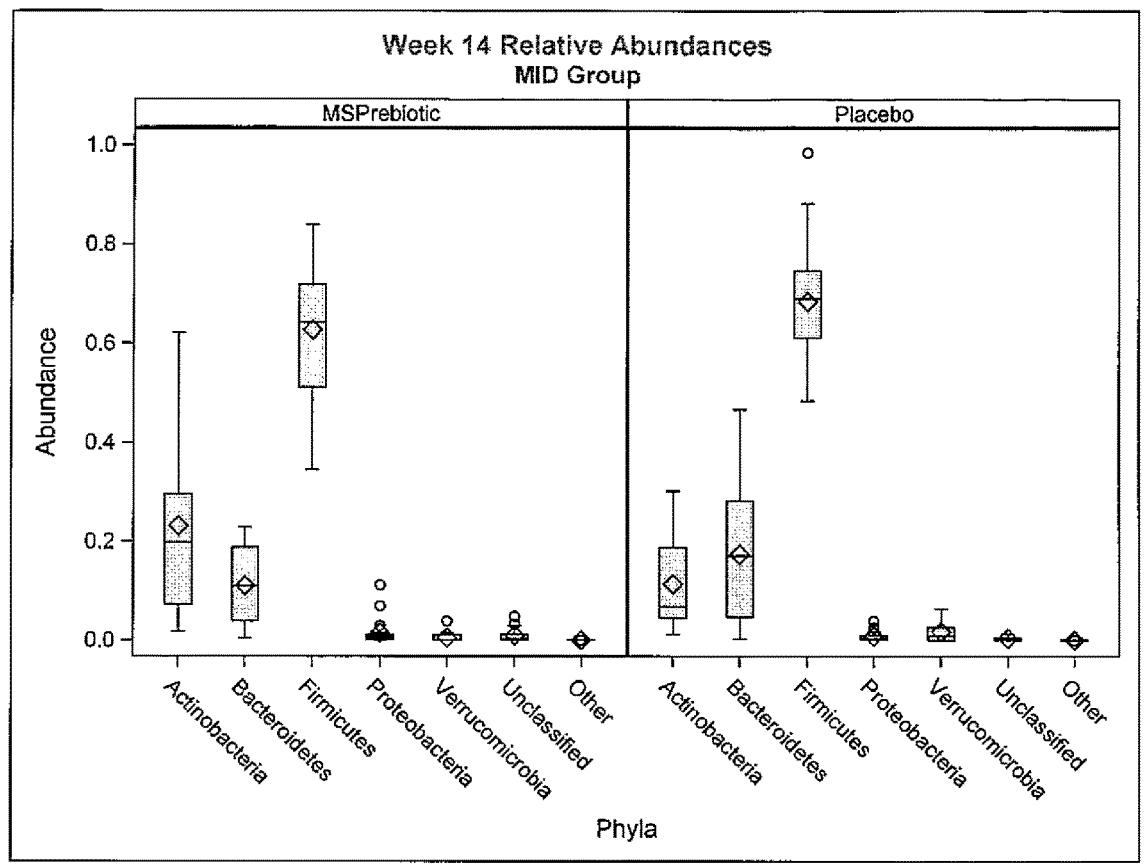
Figure 4E:
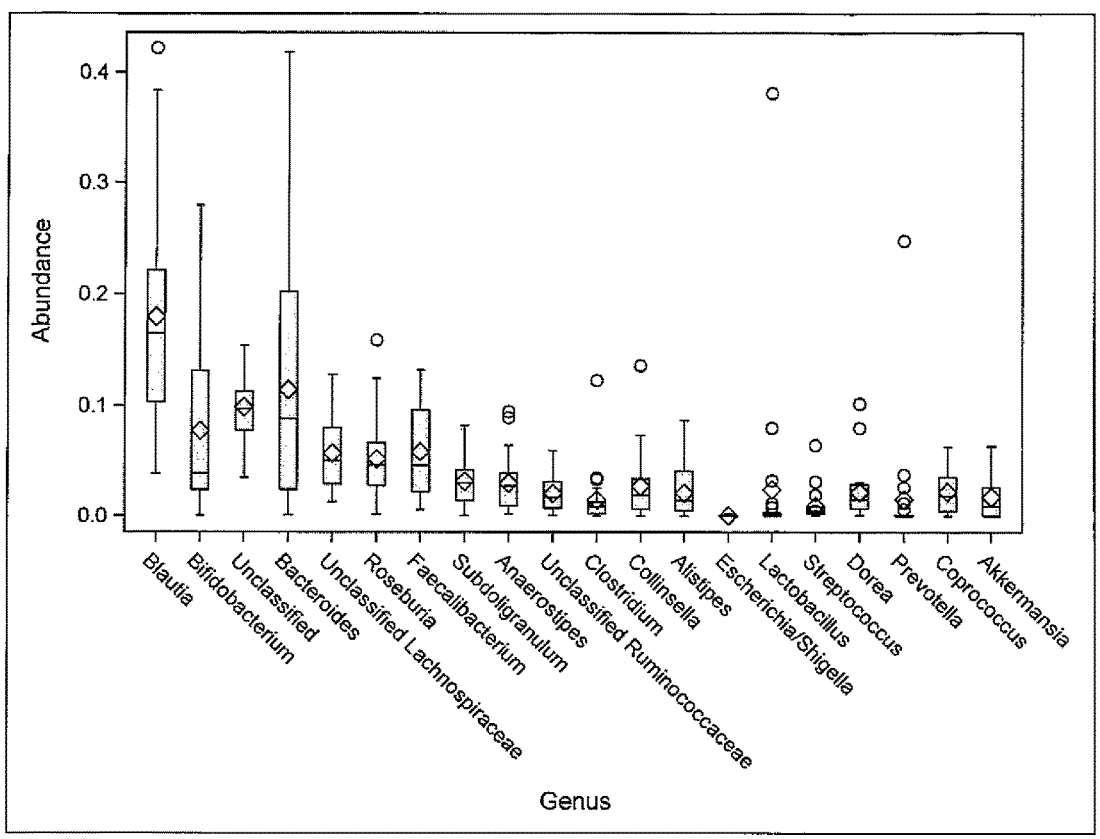
Figure 4F:
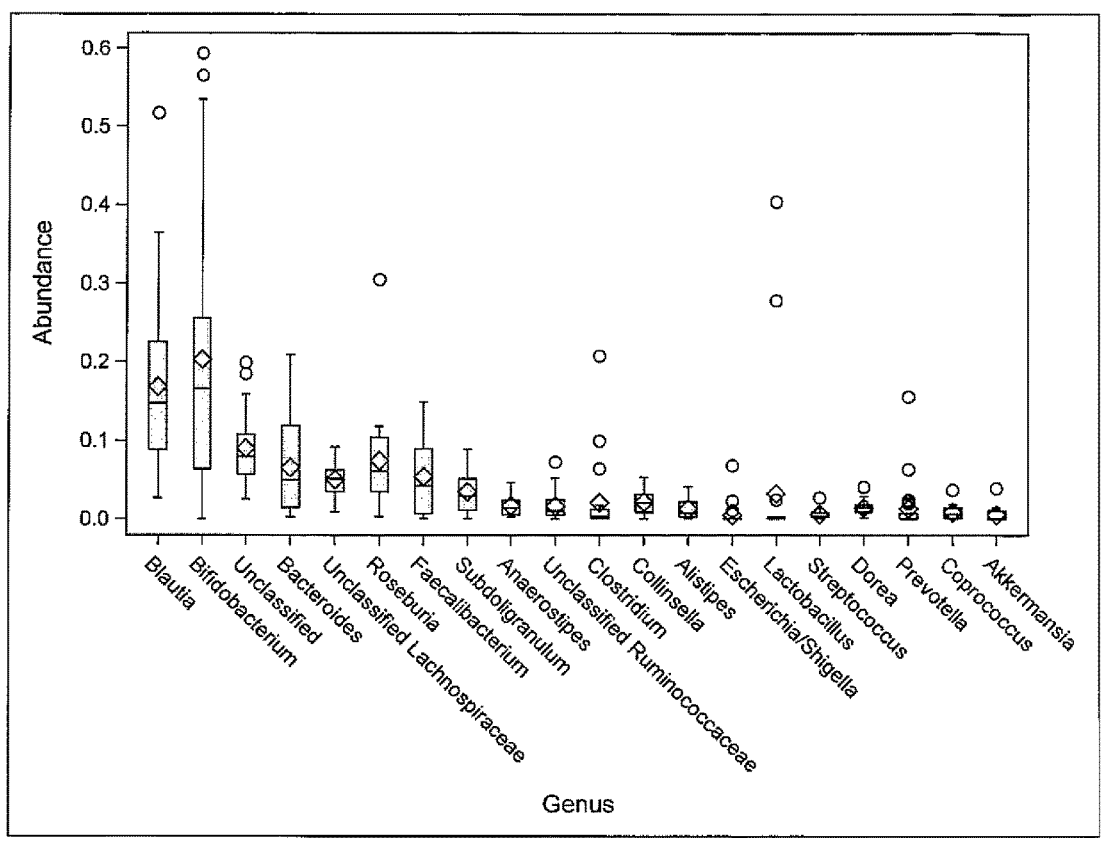

The alpha diversity plots at baseline and for the four cohorts after 12 weeks on either MSPrebiotic® or placebo are shown in FIG. 3. There were no statistically significant differences in the diversity plots at baseline; however there was a statistically significant difference in the alpha diversity plots for the Shannon and Inverse Simpson plots for ELD and MID cohorts on MSPrebiotic® compared to the placebo.

FIG. 4 shows the relative abundance of different phyla and the top 20 genera within the four cohorts at the end of the study. Statistical analysis of the impact of MSPrebiotic® versus placebo on the microbiome data at the end of the study is shown in Table 2.

Table 3 shows the breakdown of the various Bifidobacteria, *Prevotella, Alistipes* and *Desulfovibrio* species at baseline compared to after 12 weeks of consuming either placebo or MSPrebiotic®.

Table 4 shows the relative abundance of SCFAs in the stool of ELD and MID participants at baseline and after 12 weeks of consuming either placebo or MSPrebiotic®. The ELD had higher proportions of acetate and butyrate in their stool at baseline compared to MID participants where propionate represented ≥98% of the SCFAs detected.

Figure 5:
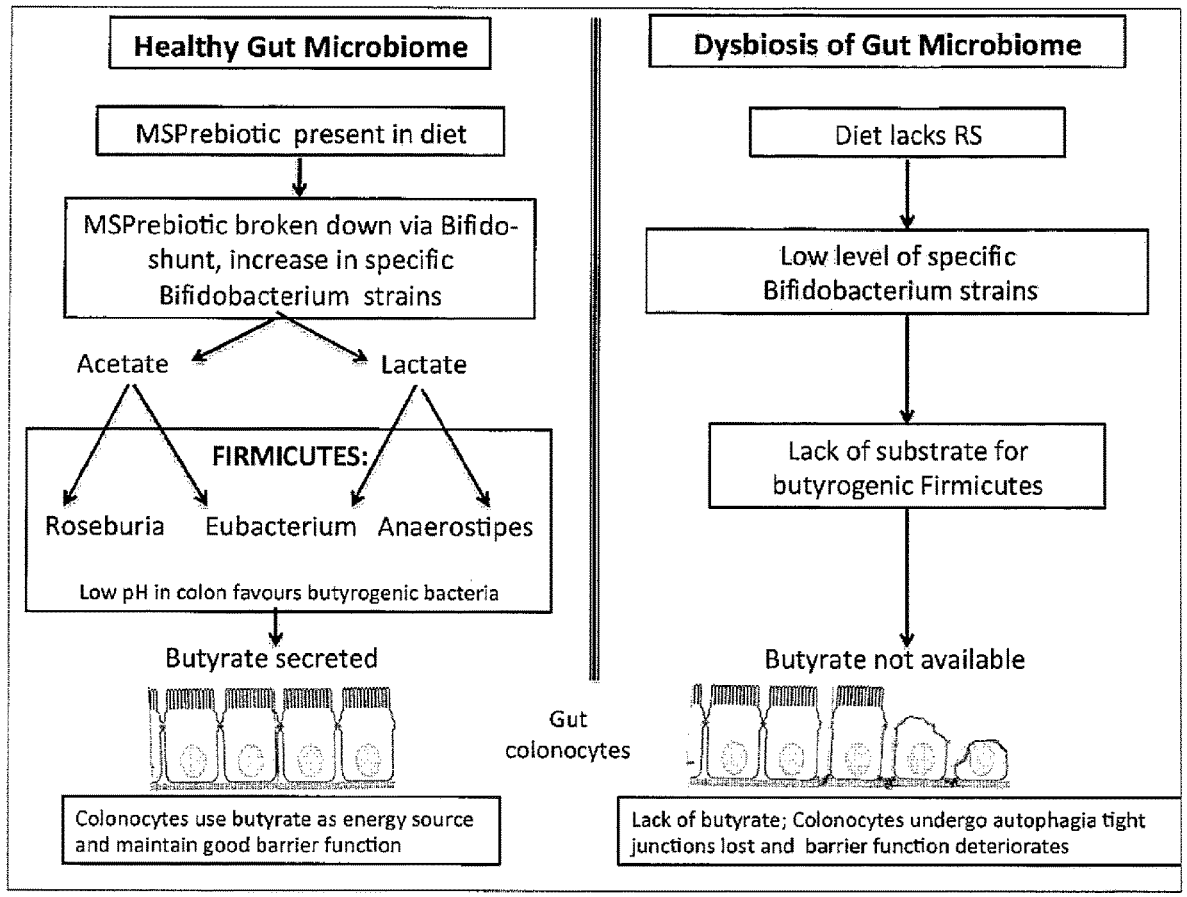
FIG. 5 Proposed cross-feeding mechanism by specific strains of Bifidobacteria provide substrate for butyrogenic Firmicutes to form butyrate. Bifidobacteria levels increase when resistant starch or other prebiotics are added to the diet. Although Bifidobacteria do not produce butyrate, their metabolic end products (acetate and lactate) are preferentially used by butryogenic strains of Firmicutes (e.g. *Roseburia, Eubacterium* and *Anaerostripes* are key butyrate producing genera with the Firmicutes Phylum). Butyrate is secreted from these Firmicutes and utilized by gut colonocytes as their primary energy source. Without butyrate to provide energy, gut colonocytes die.
Figure 6:
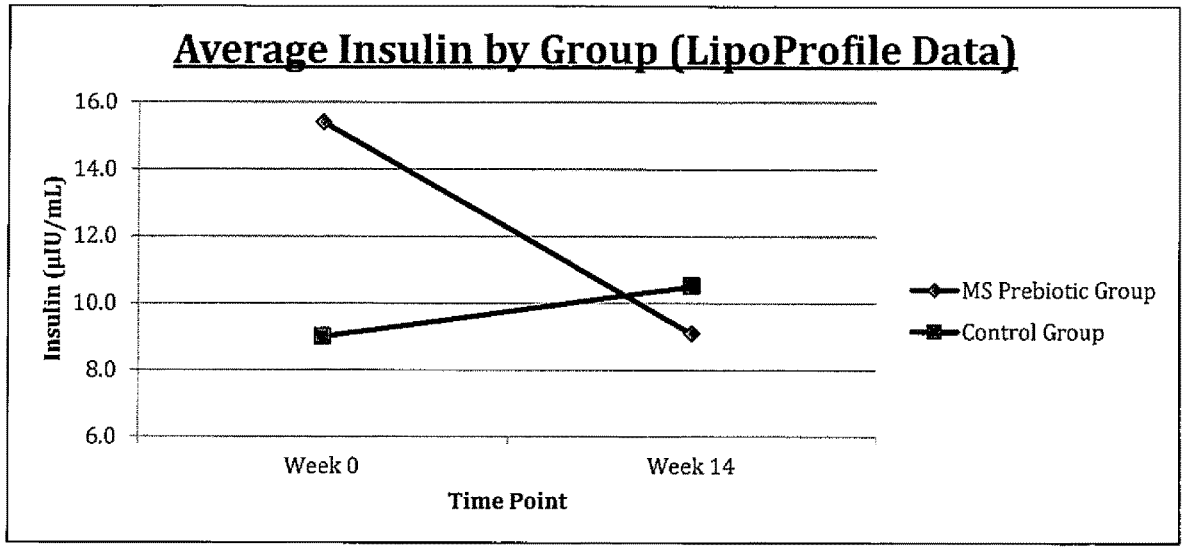
FIG. 6. Graph showing decrease in average insulin level over time for MS Prebiotic group compared to relatively constant level for control group.
Figure 7:
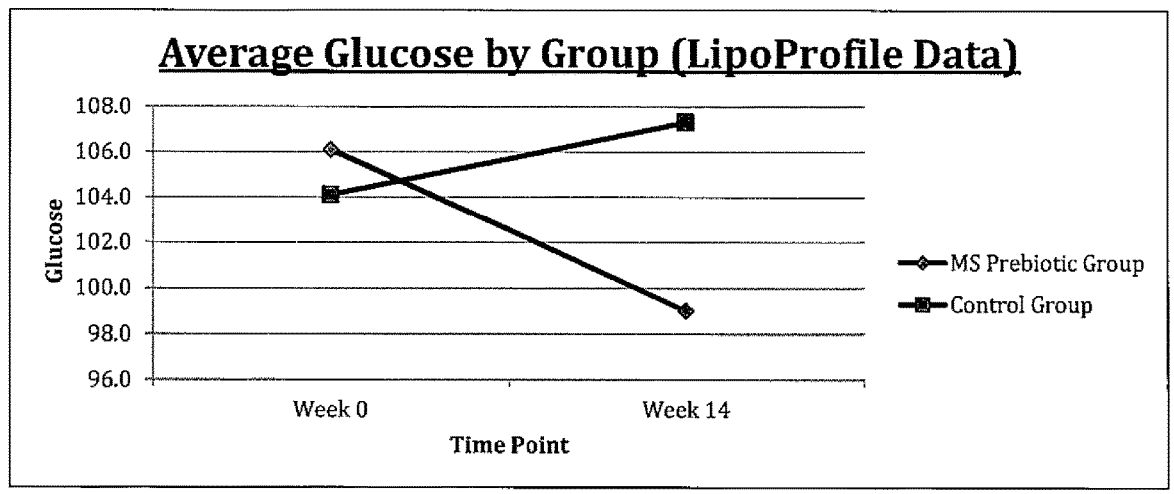
FIG. 7. Graph showing decrease in average glucose level over time for MS Prebiotic group compared to increase for control group.
Figure 8:
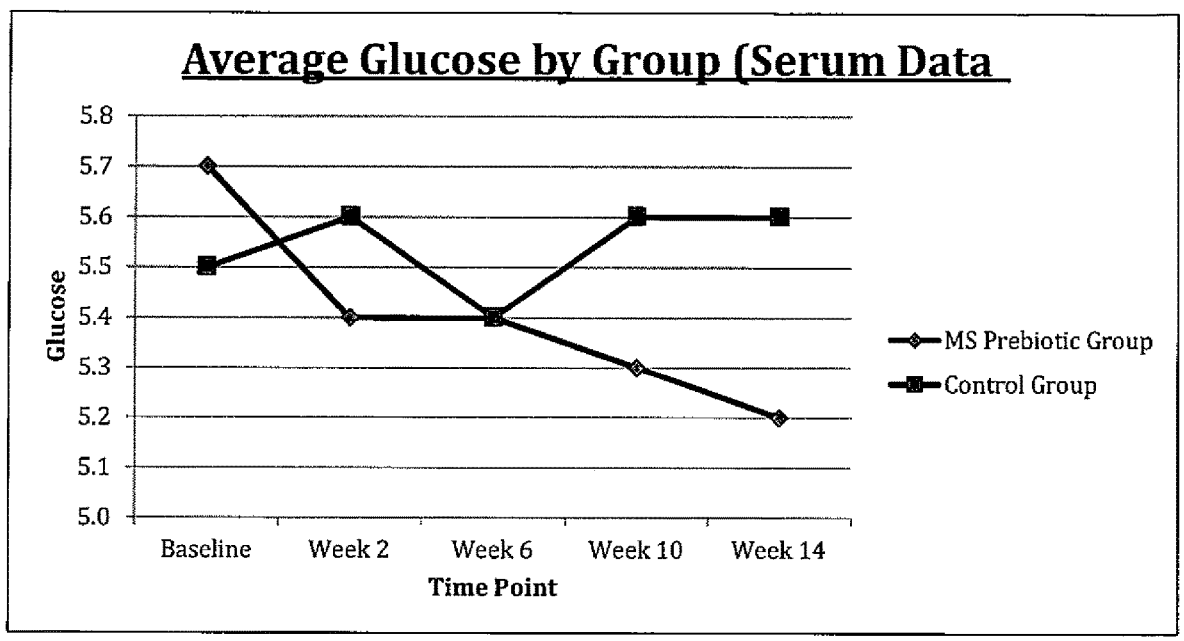
FIG. 8. Graph showing decrease in average glucose level over time for Elderly MS Prebiotic group compared to relatively constant levels for Elderly control group.

In both the ELD and MID populations on MSPrebiotic® there was a significant increase in the abundance of *Bifidobacterium* but only in the ELD was there a significant increase in the relative proportion of butyrate and only for MSPrebiotic®. FIG. 5 is a representative overview of the published data to provide a proposed explanation for how increased *Bifidobacterium* can cross-feed specific butyrate producing Firmicutes strains and lead to changes in butyrate levels needed to maintain the barrier function of gut colonocytes.

There were no significant changes in C-reactive protein, IL-10 or TNF-α in either the ELD or MID cohorts over the course of the clinical study. It is important to note however that even though inflammatory markers were not changed, the selection criteria for participants largely excluded those who might have existing inflammation, including type 2 diabetes and other inflammation-associated disorders. Secondly, it is possible that the detection of low level inflammation would require the analysis of other inflammatory markers and cytokines. There were no significant differences between placebo or MSPrebiotic® in either the ELD or MID groups with respect to; overall health, abdominal pain, bloating, flatulence or bowel movements. There was no group-time significant difference in the average number of bowel movements per day over the entire duration of the study for each group of participants. The overall average bowel movements per day was; 1.80 for ELD-MSPrebiotic®, 1.49 for ELD-placebo, 1.55 for MID-MSPrebiotic® and 1.28 for MID-placebo. However, there was a significant reduction over time in the percentage of elderly who used stool softeners at least once per week in the MSPrebiotic® group compared to the placebo (Table 5).

Power Analysis and Sample Size

For the randomized, placebo controlled study design and using the outcome measures described in the study protocol, the statistical power analysis indicated that a total sample of n=20 in each group would have a power=0.80 to detect a Cohen's F effect size=0.33 This effect size was selected under the hypothesis that moderate differences (0.50 S.D) would be observed between the placebo and treatment groups for the elderly participants and small differences (0.20 S.D.) would be observed between the placebo and treatment groups for the 30-50 year olds. It is also hypothesized that the treatment group of the elderly participants will still have a lower, but similar (0.2 S.D. difference) response level than the 30-50 year old placebo group. Effect sizes were estimated from published studies using similar outcome measures (gastrointestinal tolerance i.e. flatulence, bloating and abdominal pain and serum inflammatory marker i.e. C-reactive protein). An alpha level of p=0.05 and two-tailed tests were used in the power calculations.

Clinical Study:

This was a prospective, randomized, double-blind, placebo controlled study. All information collected and sent for statistical analysis only had a study number and no participant identifiers. All participant identifiers were treated in confidence and in accordance with the Personal Health Information Act of Manitoba.

Residents of a long term care (LTC) facility as well as independent community dwellers were recruited in Winnipeg, Manitoba, Canada. The elderly cohort consisted of adults≥70 years old (recruited from LTC and community) and mid-age participants were adults aged 30 to 50 years old (recruited from community). To ensure the microbiome changes were not due to confounding factors unrelated to consumption of digestion resistant starch (RS), there were a number of exclusion criteria including: pregnancy, Crohn's disease or any other inflammatory bowel disease, individuals with Lupus, or on cancer chemotherapy, pre-diabetes or diabetes, thyroid disease, renal disease, hepatic disease, previous gastrointestinal surgery (intestinal resection, gastric bypass, colorectal surgery), subjects on probiotic (e.g. yoghurt), subjects on antibiotics at time of recruitment or on antibiotics within the previous five weeks, individuals experiencing dysphagia, subjects using additional fiber supplements, and subjects on digestants, emetics, anti-emetics, medications for acid peptic disease or taking antacids.

The digestion resistant starch (RS) used for this clinical study was MSPrebiotic® (MSPrebiotics Inc., Carberry, Manitoba). It is an unmodified natural resistant preparation derived from potatoes that is of Natural Health Product-quality for human food application. The active ingredient in MSPrebiotic® is *Solanum tuberosum* extract which is classified as a Natural Health Product on the Health Canada website. Analytical procedures have determined that MSPrebiotic® contains 60-70% RS2. MSPrebiotic® is to be consumed in fluid or food products that are not heated. The placebo for this clinical study was Amioca TF (Ingredion™, Brampton, ON) which is a food-grade corn starch that is readily digestible and analytic testing demonstrated that it does not contain any RS. All participants consumed their normal diet and in addition consumed 30 g of placebo daily for 2 weeks and then they were randomly assigned to either MSPrebiotic® or placebo (30 g/day) for the remaining 12 weeks of the study. In the LTC facility the MSPrebiotic® or Placebo were administered following the standard administration of medication protocol using observed consumption as well as documentation using the daily health-log forms. For participants in the general population, compliance was monitored by the participant completing the daily health-log forms documenting daily consumption. In addition the amount of returned product at the monthly visits was assessed. To determine acceptability of MSPrebiotic® and placebo there was a daily health log to track excessive flatulence, changes in bowel movements, abdominal pain and bloating.

Blood and stool samples were collected as shown in FIG. 1. Blood samples were submitted to the laboratory for analysis on the day of collection. For IL-10 and TNF-α testing the blood samples were centrifuged and the plasma was dispensed into aliquots and stored at −70° C. until tested. After being frozen, aliquots were thawed once for analysis and then whatever portion of the aliquot remained was discarded. Stool was held at 4° C. in the fridge or on ice packs and transported to the laboratory usually on the same day of collection or within 72 hours if collected on the weekend. The stool was diluted 1:3 with sterile PBS to create a fecal slurry. Aliquots of the fecal slurry were frozen at −70° C. for 16S sequencing and for SCFA analysis. The aliquot was thawed only once on the day of extraction and any remaining portion was discarded.

Analysis Performed:

Blood Analysis:

Blood samples at the five collection times indicated in FIG. 1 were analyzed by the Chemistry Dept, Diagnostic Services Manitoba for: C-reactive protein. In addition blood was collected and analyzed in the research laboratory for Human IL-10 (Invitrogen, Fredrick, Md.), and TNF-α (Invitrogen).

Stool Analysis:

Feces was collected at the five collection times indicated in FIG. 1. The frozen fecal slurry aliquots were batched for short-chain-fatty-acids (SCFA) and microbiome assessment using 16S sequencing.

SCFA analysis:

The short chain fatty acid levels in feces were determined using Gas Chromatography (GC) according to the method of Stewart et al, 2010.

30 m Column Profile for SCFA Analysis:

The samples were separated on a DB225MS column (30 m×0.25 mm diameter and 0.25 μm film thickness; Agilent Technologies Canada Inc., Mississauga, Ontario) using a Varian 450 GC with FID. The temperature program was 70° C. for 1 min, the temperature was raised to 180° C. at 25° C./min, held for 1 min, raised to 200° C. at 10° C./min, held for 1 min, and raised to 220° C. at 2° C./min and held for 10 min. and finally raised to 240° C. at 20° C./min and held for 6 min. Samples were run with a 20:1 split ratio and a 1.3 ml/min column flow. Hydrogen was used as the carrier gas for the method. The temperatures of the injector and detector are 270° C. and 290° C. respectively. Peaks were verified against standards from Nu-chek Prep Inc. (Elysian, Minn.).

Microbiome Analysis by 16S Sequencing:

Sequencing:

Fecal slurries from baseline at the time of enrolment and at week 14 after 14 weeks of consuming placebo or after 2 weeks of consuming Placebo followed by 12 weeks of consuming MSPrebiotic® (FIG. 1) were thawed at 4° C. DNA templates were isolated in 96-well format using a validated protocol for ZR-96 Fecal DNA Kit (Zymo Research, Irvine, Calif.) with bead-beating. Templates were prepared as 16S rRNA V4 PCR amplicons with custom, dual-indexed-barcodes. These low-diversity, indexed amplicons underwent quality control, normalization and pooling, quantification, and final census sequencing on the Illumina MiSeq platform. Specifically, the wet lab protocol "16S Metagenomic Sequencing Library Preparation Preparing 16S Ribosomal RNA Gene Amplicons for the Illumina MiSeq System' Part #15044223 Rev. B" was followed, but with modifications to the manufacturer's guidelines [Primers 515fXT and 806rXT primers were used to target for only the V4 region; only 18 μl of 10 mM Tris pH 8.5 was added to each well of the Amplicon PCR plate to elute, with only 15 μl of the supernatant recovered. Additionally, the final V4 library size was ~420 bp; after the library size was validated, the libraries were quantitated with PicoGreen, and pooled in equimolar amounts without using more than half the volume of any sample (the pool was concentrated down if needed). The pools were gated to select for 250-650 bp fragments on a BluePippin (Sage Science) with 1.5% cassettes. Thereafter, the pools were quantified by Qubit™ 2.0 fluorometric quantitation (Thermo Fisher Scientific Inc., Waltham, Mass.) and cleaned with a final bead clean-up with 0.6× AmpureXP (Beckman Counter Canada, LP, Mississauga, ON). An Agilent Tapestation analyzer (Agilient Technologies Canada Inc., Mississauga, ON) was used to assess the size of the pooled library and its concentration, and appropriate amounts were denatured to load. Census sequencing of the 16S V4 amplicons was achieved by loading ~10 pM (for a DNA cluster density (~800-1000 k/mm$^2$), with ~21% PhiX spike-in control DNA. The MiSeq Control Software (MCS) included Real Time Analysis software (RTA), Version 1.17.28. Illumina MiSeq paired-end reads (2×300 bp) were acquired alongside a spike-in known mock community (HM-782D; BEI Resources) to assess the base calling error rate. The final data set was comprised of 6 MiSeq runs (2 runs with 24 samples multiplexed; 4 runs with 36 samples multiplexed) for a total of 188 samples, including replicates.

Data Processing:

Contig assembly (paired read set combined for each sample), quality control, and taxonomic profiling were conducted using mothur (v.1.34.0) microbiota survey analysis suite (Schloss et al 2009, Kozich et al 2013). The paired-end reads (2×300 bp) were assembled using the "make.contigs" command, generating 82,850,256 raw contigs. Contigs were filtered to exclude any low-quality contigs with average quality score<20, merged length≥315 bp, containing any ambiguous base calls, containing homopolymers of >8 nucleotides, or identified as a chimeric artifact. The average number of quality-filtered contigs per sample was determined to be 110,326 (minimum 10,914; maximum 350,889). Error rates for the sequences were assessed via the co-sequenced (known) mock community. The quality-improved contigs were aligned against the 16S rDNA SILVA database (Pruesse et al 2007); sequencing noise was reduced by clustering reads that differed by a maximum of 2 nucleotides. Contigs were binned into species-level (≥97% sequence similarity) operational taxonomic units (OTU) using the average neighbor algorithm, and taxonomically classified using the SILVA database with Ribosomal Database Project taxonomy (Wang et al 2007) and a 60% minimum bootstrap. Species counts were generated using SPINGO software (Allard et al 2015) with default parameters and a minimum 60% bootstrap cutoff for the species level.

Statistical Analysis:

Microbiome data at the phylum and genus levels were compared between treatment and age groups using 64-bit R version 3.2.5 (R Core Team (2016) R Foundation for Statistical Computing, Vienna, Austria) with the Phyloseq (McMurdie et al 2013) and DESeq2 (Love et al 2014) packages. Phyloseq was used for data pre-processing, graphing, and the calculation of alpha diversity measures. Average diversity was compared between groups using analysis of variance (ANOVA). OTU abundance was compared between groups using DESeq2 (Love et al 2014), a method for differential analysis of high-throughput count data based on a negative binomial regression model. Information was shared across OTUs through empirical Bayes shrinkage estimation for the relative abundance variance and ratio estimates, improving stability for rare OTUs with low counts. DESeq2 (Love et al 2014) also provides protection against false positives via independence filtering and false discovery rate p value adjustment, which is necessary given the large number of hypothesis tests conducted for microbiome data. Raw counts were used for the OTU analysis instead of relative abundance percentages, as the latter loses information on read size and therefore on statistical uncertainty. Similarly, abundance data were not rarefied prior to analysis, as this approach is statistically inefficient (McMurdie et al 2013). These steps are not necessary since different read sample size is naturally accounted for in the negative binomial modeling framework. Singletons were removed prior to analysis. OTU relative abundance comparisons are presented as base 2 logarithmic fold change along with their corresponding p values.

Inflammatory Markers and Other Primary Outcome Markers:

Differences between groups for continuous variables were analyzed by a two-way factorial repeated measures ANOVA. The between subjects factors are group (placebo and treatment group) and age (elderly vs. adult) and the within subjects repeated measure factor is time (baseline, 2 weeks after placebo and 4, 8 and 12 weeks after randomization). Data are expressed as means±standard error. Post-hoc comparisons were made using Tukey's multiple comparison tests. The level of statistical significance for all analysis is $p<0.05$ (two-tailed tests were employed). The relationship between MSPrebiotic® and the primary outcome measures was analyzed by point-biserial correlation coefficients. The scores of efficacy and the intensity and frequency of the gastrointestinal symptoms were evaluated as compared to baseline values by Mann-Whitney-Wilcoxon rank test.

The scope of the claims should not be limited by the preferred embodiments set forth in the examples, but should be given the broadest interpretation consistent with the description as a whole.

REFERENCES

1. Allard G, Ryan F J, Jeffery I B, Claesson M J. SPINGO: a rapid species-classifier for microbial amplicon sequences. BMC Bioinformatics 2015; 16:324. DOI 10.1186/s12859-015-0747-1
2. Antharam V C, Li E, Ishmael A, Sharma A, Mai V, Rand K H, Wang G P Intestinal dysbiosis and depletion of butyrongenic bacteria in *Clostridium difficile* infection and nosocomial diarrhea. J Clin Microbiol 2013 doi: 10.1128/JCM.00845-13
3. Balakrishnan M, Floch M H Prebiotics, probiotics and digestive health Curr Opin Clin Nutr Metab Care 2012; 4 doi:10.1097/MCO.0b013e328359684f
4. Biagi E, Candela M, Fairweather-Tait S, Franceschi C, Brigidi P Aging of the human metaorganism: the microbial counterpart. AGE 2012; 34:247-267 DOI: 10.1007/s11357-011-9217-5
5. Bien J, Palagani V, Bozko P The intestinal microbiota dysbiosis and *Clostridium difficile* infection: is there a relationship with inflammatory bowel disease? Ther Adv Gastroenterol 2013; 61:53-68 DOI: 10.1177/1756283X12454590
6. Brown K, DeCoffe D, Molcan E, Gibson D L Diest-induced dysbiosis of the microbiota and the effects on immunity and disease. Nutrients 2012; 4:1095-1119, DOI: 10.3390/nu40810951
7. Cecchini D A, Laville E, Laguerre 5, Robe P, Leclerc M, Dore J, Henrissat B, Remaud-Simeon M, Monsan P, Potocki-Veronese G Functional metagenomics reveals novel pathways of prebiotic breakdown in human gut bacteria. PLOS one 2013; 8:e72766. Doi:10.1371/journal.pone.0072766
8. Claesson M J, Cusack S, O'Sullivan O, Greene-Diniz R, de Weerd H, Flannery E, Marchesi J R, Falush D, Dinan T, Fitzgerald G, Stanton C, van Sinderen D, O'Connor M, Harnedy N, O'Connor K, Henry C, O'Mahony I D et al Composition, variability, and temporal stability of the intestinal microbiota of the elderly. PNAS 2011; 108 4586-4591 DOI: 10.1073/pnas.1000097107
9. Claesson M J, Jeffery I B, Conde S, Power S E, O'Connor E M, Cusack S, Harris H M B, Coakley M, Lakshminarayanan B, O'Sullivan O, Fitzgerald G F, Deane J, O'Connor M et al. Gut microbiota composition correlates with diet and health in the elderly. Nature 2012; 488:178-185 DOI: 10.1038/nature11319
10. Delzenne N M, Neyrinck A M, Cani P D Modulation of the gut microbiota by nutrients with prebiotic properties: consequences for host health in the context of obesity and metabolic syndrome Microbial Cell Factories 2011; 10(Suppl 1):510 DOI: 10.1186/1475-2859-10-S1-S10.
11. Dethlefsen L, Reiman D A Incomplete recovery and individualized response of the human distal gut microbiota to repeated antibiotic perturbation. PNAS 2011; 108: DOI: 10.1073/pnas.1000087107/-/DCSupplemental
12. Donohoe D R, Garge N, Zhang X, Sun W, O'Connell T M, Bunger M K, Bultman S J The Microbiome and butyrate regulate energy metabolism and autophagy in the mammalian colon. Cell Metab 2011; 13:517-526 DOI: 10.1016/j.cmet.2011.02.018
13. Flint H J, Scott K P, Duncan S H, Louis P, Forano E. Microbial degradation of complex carbohydrates in the gut. Gut Microbes 2012; 34:289-306
14. Hardy H, Harris J, Lyon E, Beal J, Foey A D Probiotics, prebiotics and immunomodulation of gut mucosal defences: homeostasis and immunopathology. Nutrients 2013; 5:1869-1912, doi:10.3390/nu5061869
15. Health Canada Natural Health Product website: (http://webprod.hc-sc.gc.ca/nhpid-bdipsn/ingredReq.do?id=6482&lang=eng *Solanum Tuberosum* Extract)
16. Holmes Elaine, Kinross J, Gibson G R, Burcelin R, Jia W, Pettersson S, Nicholson J K Therapeutic modulation of microbiota-host metabolic interactions. Sci Transl Med 2012; 4:137rv6DOI:10.1126/scitranslmed.3004244
17. Illumina 16S Sequencing Laboratory Protocol: http://support.illumina.com/content/dam/illumine-support/documents/documentation/chemistry_documentation/16s/16metagen omic-library-prep-guide-15044223-b.pdf
18. Kleessen B, Sykura B, Zunft H-J, Blaut M Effects of inulin and lactose on fecal microflora, microbial activity, and bowel habit in elderly constipated persons Am J Clin Nutr 1997; 65:1397-1402
19. Kolanowski A, Mulhall P, Yevchak A et al The triple challenge of recruiting older adults with dementia and high medical acuity in skilled nursing facilities. J Nursing Scholarship 2013; 45:397-404.
20. Kozich J J, Westcott S L, Baxter N T, Highlander S K, Schloss P D Development of a dual-index sequencing strategy and curation pipeline for analyzing amplicon sequence data on the MiSeq Illumina sequencing platform. Applied and Environmental Microbiology. 2013; 79(17):5112-20.
21. Malaguarnera A, Leggio F, Vacante M, Motta M, Giordano M, Biondi A Basile F, Mastronjeni S, Mistretta A, Malaguarnera M Toscano M A, Salmeri M Probiotics in the gastrointestinal diseases of the elderly. J Nutr Health Aging
22. Mariat D, Firmesse O, Levenez F, Guimaracs V D, Sokol H, Dore J, Corthier G, Furet J P the Firmicutes/Bacteroidetes ratio of the human microbiota changes with age. BMC Microbiol 2009; 9:123.

23. Martinez I, Kim J, Duffy P R, Schlegel V L, Walter J Resistant starches types 2 and 4 Have differential effects on the composition of the fecal microbiota in human subjects. PLOSone 2010; 5(11):e15046 DOI: 10.1371/journal.pone.0015046
24. McMurdie P J, Holmes S. Phyloseq: an r package for reproducible interactive analysis and graphics of microbiome census data. PLoS One. 2013; 8: e61217.
25. Nofrarias M, Martinez-Puig D, Pujols J, Majo N, Perez J F Long-term intake of resistant starch improves mucosal integrity and reduces gut apoptosis and blood immune cells. Nutrition 2007; 23:861-870
26. O'Keefe S J D Tube feeding, the microbiota, and *Clostridium difficile* infection. World J Gasgroenterol 2010; 16:139-142. DOI:10.3748/wjg.v16.12.139
27. Patel R, DuPont H L New approaches for bacteriotherapy: Prebiotics, new-generation probiotics and synbiotics. CID 2015; 60(S2):S108-121.
28. Patel S, Goyal A The current trends and future perspectives of prebiotics research: a review. 3 Biotech 2012; 2:115-125 DOI: 10.1007s13205-012-0044-x
29. Pokusaeva K, Fitzgerald G F, van Sinderen D Carbohydrate metabolism in Bifidobacteria. Genes Nutr 2011; 6:285-306 DOI: 10.1007/s12263-010-0206-6
30. Priebe M G, Vonk R J, Sun X, He T, Harmsen M J M, Welling G W The physiology of colonic metabolism. Possibilities for interventions with pre- and probiotics. Eur J Nutr 2002; 41(Suppl 1), DOI:10.1007/s00394-002-1101-8
31. Pruesse E, Quast C, Knittel K, et al. SILVA: a comprehensive online resource for quality checked and aligned ribosomal RNA sequence data compatible with ARB. Nucleic Acids Res. 2007; 35:7188-7196.
32. Saraswati S, Sitaraman R Aging and the human gut microbiota—from correlation to causality. Frontiers in Microbiology 2015; 5:1-4 (article 764)
33. Schloss P D, Westcott S L, Ryabin T, et al. Introducing mothur: open-source, platform-independent, community-supported software for describing and comparing microbial communities. Appl Environ Microbiol. 2009; 75:7537-7541.
34. Schneider S M, Girard-Pipau F, Anty R, van der Linde E G M, Philipsen-Geerling B J, Knol J, Filippi J, Arab K, Hebuterne X Effects of total enteral nutrition supplemented with a multi-fibre mix on faecal short-chain fatty acids and microbiota. Clin Nutri 2006; 25:82-90
35. Stewart M L, Nikhanj S D, Timm D A, Thomas W, Slavin J L Evaluation of the effect of four fibers on laxation, gastrointestinal tolerance and serum markers in health humans. Ann Nutr Metab 2010; 56:91-98; doi: 10.1159/000275962
36. Topping D L, Clifton P M Short-chain fatty acids and human colonic function: Roles of resistant starch and nonstarch polysaccharides Physiological Reviews 2001; 81:1031-1064
37. Toward R E, Montandon S L, Walton G E, Gibson G R Effect of prebiotics on the human gut microbiota of elderly persons. Gut Microbes 2012; 3:57-60 DOI: 10.4161/gmic.19411
38. Wang Q, Garrity G M, Tiedje J M, et al. Naïve Bayesian classifier for rapid assignment of rRNA sequences into the new bacterial taxonomy. Appl Environ Microbiol. 2007; 73:5261-5267.
39. Wang, X, Conway P L, Brown I L, Evans A J In Vitro utilization of amylopectin and high-amylose maize (amylomaize) starch granules by human colonic bacteria. Applied Environmental Microbiol 1999; 65:4848-4854.
40. Ze X, Duncan S H, Louis P, Flint H J *Ruminococcus bromii* is a keystone species for the degradation of resistant starch in the human colon. ISME Journal 2012; 6:1535-1543
41. Zhernakova A, Kurilshikov A, Bonder M J, Tigchelaar E T et al Population-based metagenomics analysis reveals markers for gut microiome composition and diversity. Science 2016; 352:565-569. Doi: 10.1126/science.aad3369.
42. Moya-Perez A, Neef A, Sanz Y, *Bifidobacterium pseudocatenulatun* CECT 7765 Reduces Obesity-Associated Inflammation by Restoring the Lymphocyte-Macrophage Balance and Gut Microbiota. PLoS One 2015 Jul. 10:10 (7).
43. O'Callaghan A, van Sinderen D, Bifidobacteria and Their Role as Members of the Human Gut Microbiota, Microbiota. Front. Microbiol. 2016; 7:925.
44. Hopkins M, Sharp R, MacFarlane, G, Age and disease related changes in intestinal bacterial populations assessed by cell culture, 16S rRNA abundance, and community cellular fatty acid profiles. Gut 2001 48: 198-205.
45. Satokari R M, Vaughn E E, Smidt H et al., Molecular approaches for the detection and identification of bifidobacteria and lactobacilli in the human gastrointestinal tract. Syst. Appl. Microbiol. 2003 26:572-584.
46. Petersen C, Round J L, Defining dysbiosis and its influence on host immunity and disease, Cellular Microbiology 2014 16(7): 1024-1033.
47. Lin H V et al., Butyrate and propionate protect against diet-induced obesity and regulate gut hormones via free fatty acid receptor 3-independent mechanisms, PLoS One 2012 7:4.
48. Malcomson F C et al., Is resistant starch protective against colorectal cancer via modulation of the WNT signaling pathway?, Proceedings of the Nutrition Society 2015 74: 282-291.
49. Arumugam et al., Enterotypes of the human gut microbiome, Nature 2011 473: 174-180.
50. Love M I, Huber W, Anders S. Moderated estimation of fold change and dispersion for RNA-Seq data with DESeq2. Genome Biol 2014; 15:550.

TABLE 1

Comparison of phyla and genera in elderly and mid-age groups at baseline.

| Phylum: | Order | Genus | $\text{Log}_2$ fold difference:[1] | $p_{adjusted}$:[3] |
|---|---|---|---|---|
| Firmicutes | | | −0.4419 | 0.0236 |
| | Clostridiales | Ruminococcaeae | −2.0054 | <0.001 |
| | Clostridiales | Dialister | 1.5403 | 0.075 |
| | Clostridiales | Megasphaera | 7.5027 | <0.001 |
| | Erysipelotrichales | Catenibacterium | 3.6167 | 0.001 |

TABLE 1-continued

Comparison of phyla and genera in elderly and mid-age groups at baseline.

| Phylum: | Order | Genus | Log$_2$ fold difference:[1] | p$_{adjusted}$:[3] |
|---|---|---|---|---|
| Bacteroidetes | | | −0.4780 | 0.1572 |
| | Bacteroidales | *Prevotella* | 1.7937 | 0.092 |
| | Bacteroidales | *Bacteroides* | −1.7369 | 0.006 |
| Actinobacteria | | | 0.3521 | 0.1572 |
| | Coriobacteriales | *Eggerthella* | −1.152 | 0.119 |
| Proteobacteria | | | −2.3022 | <0.001 |
| | Enterobacteriales | *Escherichia/ Shigella* | −3.1199 | <0.001 |
| Verrucomicrobia | | | −1.8856 | 0.0023 |
| | Verrucomicrobiales | *Akkermansia* | −1.5072 | 0.039 |

[1] Analysis done using DESeq2 package with ELD as the comparator. Negative values indicate MID had lower abundance compared to ELD and positive values indicate MID had higher abundance compared to ELD.
[3] Adjusted p value; accounts for repeated measures and reduces the false detection rate.

TABLE 2

Differences between genera in elderly and mid-age groups after 12 weeks of consumption of MSPrebiotic ® versus Placebo.

| Phylum: | Order | Genus | Log$_2$ fold change[1] | Padjusted:[2] |
|---|---|---|---|---|
| ELDERLY GROUP comparison: MSPrebiotic ®/Placebo | | | | |
| Actinobacteria | Bifidobacteriales | *Bifidobacterium* | 1.8485 | 0.049 |
| Bacteroidetes | Bacteroidetes | *Prevotella* | 3.5696 | 0.005 |
| | Bacteroidetes | *Alistipes* | 1.4092 | 0.030 |
| Proteobacteria | Desulfovibrionales | *Desulfovibrio* | 5.6677 | <0.001 |
| Firmicutes | Clostridiales | *Mogibacterium* | 2.7243 | 0.024 |
| | Clostridiales | *Sporobacter* | 3.0079 | 0.001 |
| MID-AGE GROUP Comparison: MSPrebiotic ®/Placebo | | | | |
| Actinobacteria | Bifidobacteriales | *Bifidobacterium* | 1.5487 | 0.002 |
| | Coriobacteriales | *Olsenella* | 2.5354 | <0.001 |
| Firmicutes | Erysipelotrichaceae | *Coprobacillus* | −2.2679 | 0.047 |
| | Lactobacillales | *Lactobacilllus* | −1.96097 | 0.003 |

[1] Analysis done using DESeq2 package with Placebo as the comparator (ie. demoninator). Negative values indicate MSPrebiotic ® had lower abundance compared to Placebo and positive values indicate MSPrebiotic ® had higher abundance compared to Placebo.
[2] Adjusted p value; accounts for repeated measures and reduces the false detection rate.

TABLE 3

Relative distribution of species within the various genera
Percentage of each species within the genus[1]

| | BASELINE | | PLACEBO | | MSPREBIOTIC ® | |
|---|---|---|---|---|---|---|
| | MID | ELD | MID | ELD | MID | ELD |
| *Bifidobacterium* genus: | | | | | | |
| *B. adolescentis* | 1.05 | 0.86 | 2.30 | 1.15 | 5.07 | 4.32 |
| *B. animalis* | 0.00 | 0.17 | 0.00 | 0.00 | 0.00 | 0.00 |
| *B. bifidum* | 65.57 | 42.29 | 72.94 | 48.85 | 66.67 | 44.14 |
| *B. boum* | 0.00 | 0.17 | 0.00 | 1.72 | 0.00 | 0.00 |
| *B. breve* | 2.33 | 3.25 | 1.76 | 4.89 | 3.12 | 4.63 |
| *B. catenulatum* | 0.00 | 0.00 | 0.00 | 0.00 | 0.19 | 0.00 |
| *B. dentium* | 25.82 | 46.23 | 13.67 | 34.20 | 15.59 | 29.32 |
| *B. longum* | 0.72 | 2.05 | 3.25 | 1.72 | 1.36 | 4.63 |
| *B. mongoliense* | 0.16 | 0.00 | 0.00 | 0.00 | 0.58 | 0.00 |
| *B. pseudocatenulatum* | 3.30 | 4.79 | 4.74 | 4.89 | 2.53 | 10.49 |
| *B. ruminantium* | 0.80 | 0.17 | 1.08 | 2.59 | 4.87 | 2.47 |
| *B. stellenboschense* | 0.08 | 0.00 | 0.00 | 0.00 | 0.00 | 0.00 |

TABLE 3-continued

Relative distribution of species within the various genera
Percentage of each species within the genus[1]

| | BASELINE | | PLACEBO | | MSPREBIOTIC ® | |
|---|---|---|---|---|---|---|
| | MID | ELD | MID | ELD | MID | ELD |
| B. saguini | 0.00 | 0.00 | 0.14 | 0.00 | 0.00 | 0.00 |
| B. tsurumiense | 0.16 | 0.00 | 0.14 | 0.00 | 0.00 | 0.00 |
| Total Number: | 1243 | 584 | 739 | 348 | 513 | 324 |
| *Prevotella* genus: | | | | | | |
| P. bucae | | 0.090 | | | | 0.075 |
| P. buccalis | | 0.407 | | | | 0.896 |
| P. copri | | 82.295 | | | | 89.619 |
| P. coporis | | 0.181 | | | | 0.075 |
| P. denticla | | 1.626 | | | | 0.373 |
| P. oris | | 0.858 | | | | 0.373 |
| P. stercorea | | 14.137 | | | | 8.364 |
| P. timorensis | | 0.407 | | | | 0.075 |
| P. disiens | | 0.000 | | | | 0.149 |
| *Alistipes* genera: | | | | | | |
| A. finegoldii | | 23.356 | | | | 16.661 |
| A. indistinctus | | 10.787 | | | | 12.343 |
| A. massillensis | | 4.513 | | | | 2.113 |
| A. putredinis | | 41.267 | | | | 41.684 |
| A. senegalensis | | 4.837 | | | | 1.654 |
| A. shahii | | 15.239 | | | | 25.544 |
| *Desulfovibrio* genera | | | | | | |
| D. desulfuricans | | 0.000 | | | | 0.309 |
| D. fairfieldensis | | 13.393 | | | | 1.852 |
| D. piger | | 86.607 | | | | 97.839 |

[1]Analysis done using SPINGO package (Allard et al 2015) to provide the total number of each species using a minimum 60% bootstrap. The percentages shown are based on the total number of species within the specific genera indicated.

TABLE 4

Relative abundance of Short Chain Fatty Acids in stool at baseline and after 12 weeks of consumption of MSPrebiotic ® or Placebo

| | Baseline: | | 12 weeks of: | |
|---|---|---|---|---|
| SCFA: | Placebo | MSPrebiotic ® | Placebo | MSPrebiotic ® |
| Elderly Group: Relative % of total SCFA content (standard deviation) | | | | |
| C3: Acetate | 25.8% (21.1) | 20.5% (13.8) | 24.6% (19.1) | 21.3% (12.1) |
| C4: Butyrate | 1.8% (1.2) | 1.8% (1.4) | 1.5% (0.7) | 2.2% (1.6)* |
| C5: Propionate | 72.5% (21.4) | 79.8% (15) | 75.2 (19.5) | 79.7 (14.3) |
| Mid-Age Group: Relative % of total SCFA content (standard deviation) | | | | |
| C3: Acetate | 1.4% (2.1) | 2.3% (5.9) | 0.7% (0.6) | 0.8% (0.9) |
| C4: Butyrate | 0.1% (0.1) | 0.1% (0.1) | 0.4% (1.0) | 0.3% (1.1) |
| C5: Propionate | 98.5% (2.1) | 97.7% (5.9) | 98.9% (1.3) | 98.9% (1.4) |

*Significant increase in the C4 proportion-change of SCFAs from baseline to end of treatment in the ELD MSPrebiotic ® group compared to the ELD Placebo group ($p = 0.0219$ using the Mann-Whitney non-parametric test).

TABLE 5

Use of stool softeners in ELD and MID at baseline and once randomized to placebo or MSPrebiotic ®

| | Percentage that used stool softeners at least once/week | | | |
|---|---|---|---|---|
| | ELD[2] | | MID | |
| Week[1]: | Placebo | MSPrebiotic ® | Placebo | MSPrebiotic ® |
| 1 | 10.5% | 27.3% | 0.0% | 0.0% |
| 2 | 10.5% | 30.0% | 0.0% | 0.0% |
| 3 | 15.8% | 36.4% | 0.0% | 0.0% |
| 4 | 16.7% | 33.3% | 0.0% | 0.0% |
| 5 | 15.8% | 36.4% | 0.0% | 0.0% |
| 6 | 10.5% | 31.8% | 0.0% | 0.0% |

TABLE 5-continued

Use of stool softeners in ELD and MID at baseline and
once randomized to placebo or MSPrebiotic ®

Percentage that used stool softeners at least once/week

| Week[1]: | ELD[2] | | MID | |
|---|---|---|---|---|
| | Placebo | MSPrebiotic ® | Placebo | MSPrebiotic ® |
| 7 | 5.9% | 30.0% | 0.0% | 0.0% |
| 8 | 5.6% | 20.0% | 0.0% | 0.0% |
| 9 | 10.5% | 23.8% | 0.0% | 0.0% |
| 10 | 5.6% | 16.7% | 0.0% | 0.0% |
| 11 | 10.5% | 22.2% | 0.0% | 0.0% |
| 12 | 17.7% | 23.8% | 0.0% | 0.0% |
| 13 | 11.1% | 30.0% | 0.0% | 0.0% |
| 14 | 15.8% | 30.0% | 0.0% | 0.0% |

[1]Note:
for week 1 and 2 ALL participants were on Placebo, subsequently at the beginning of week 3 participants were randomized to receive Placebo or MSPrebiotic ®.
[2]There was a significant reduction in the use of stool softeners over time in the ELD-MSPrebiotic ® group compared to the ELD-Placebo group (Group/time interaction: p = 0.048, Beta; −0.2024, Std Error; 0.1022).

The invention claimed is:

1. A method of promoting a symbiotic or non-dysbiotic gut microbiome profile in an individual having a dysbiotic gut microbiome profile-comprising administering to said individual an effective amount of an unmodified RS type 2 potato starch preparation that is at least 60% resistant starch on a dosage regimen, said individual having a dvsbiotic gut microbiome profile that is characterized by: a loss of beneficial microbial organisms within the gut microbiome, outgrowth of pathogenic micro-organisms within the gut microbiome, and/or a loss of overall microbial diversity in the gut microbiome compared to the gut microbiome profile of a control individual or compared to the gut microbiome profile that the said individual had when younger.

2. The method according to claim 1 wherein the individual having a dysbiotic gut microbiome profile is selected from the group consisting of: an individual who is being treated with oral antibiotics; an individual who is hospitalized; an individual resides in a long term care facility; an individual suffering from irritable bowel syndrome, colorectal cancer, allergy, Coeliac disease, *Clostridium difficile* disease, inflammatory bowel disease, Crohn's disease or ulcerative colitis; an individual suffering from a disease caused by Shiga toxin; and an elderly individual.

3. The method according to claim 1 wherein the individual in need of such treatment has been diagnosed with a dysbiotic gut microbiome.

4. The method according to claim 3 wherein the individual is diagnosed with a dysbiotic gut microbiome by a method comprising:
measuring the populations of Firmicutes and/or Bacteriodetes in the gut microbiome of the individual;
measuring the populations of Firmicutes and/or Bacteriodetes in the gut microbiome of a control individual; and
comparing the populations;
wherein if the Firmicutes and/or Bacteriodetes population in the gut microbiome of the individual differs from the Firmicutes and/or Bacteriodetes population in the gut microbiome of the control individual, the individual is dysbiotic.

5. The method according to claim 3 wherein the individual is diagnosed with a dysbiotic gut microbiome by a method comprising:
measuring populations of *Bifidobacterium* in the gut microbiome of the individual;
measuring the populations of *Bifidobacterium* in the gut microbiome of a control individual; and
comparing the populations;
wherein if said individual has low levels of *Bifidobacterium* in their gut microbiome compared to the control individual, the individual has a dysbiotic gut microbiome.

6. The method according to claim 3 wherein the individual is diagnosed with a dysbiotic gut microbiome by a method comprising:
measuring populations of *Bifidobacterium* in the gut microbiome of the individual;
wherein if the gut microbiome of the individual has less than 5% bifidobacterial content, the individual has a dysbiotic gut microbiome.

7. The method according to claim 1 wherein the effective amount of the unmodified RS type 2 potato starch preparation that is at least 60% resistant starch is 0.25-40 g.

8. The method according to claim 7 wherein administering the effective amount of the unmodified RS type 2 potato starch preparation that is at least 60% resistant starch on the dosage regimen promotes a symbiotic or non-dysbiotic gut microbiome profile by increasing levels of Actinobacteria and/or Bacteroidetes in the gut microbiome of the individual.

9. The method according to claim 7 wherein administering the effective amount of the unmodified RS type 2 potato starch preparation that is at least 60% resistant starch on the dosage regimen promotes a symbiotic or non-dysbiotic gut microbiome profile by stimulating growth of endogenous *B. adolescentis*, *B. pseudocatenulatum* and/or *B. ruminantium* in the gut microbiome of the individual.

10. The method according to claim 9 with the proviso that no probiotic is administered with the unmodified RS type 2 potato starch preparation that is at least 60% resistant starch.

11. The method according to claim 1 wherein a probiotic is coadministered with the unmodified RS type 2 potato starch preparation that is at least 60% resistant starch.

12. The method according to claim 11 wherein the probiotic is selected from the group consisting of *L. acidophilus*; *L. fermentum*; *L. plantarum*; *L. rhamnosus*; *L. salivarius*; *L. paracasei*; *L. reuteri*; *B. bifidum*; *B. adolescentis*; *B. longum*; *B. pseudocatenulatum*; and *B. ruminantium*.

13. The method according to claim 7 wherein administering the effective amount of the unmodified RS type 2 potato starch preparation that is at least 60% resistant starch on the dosage regimen increases butyrate levels available for colon cells of the individual.

14. The method according to claim 7 wherein administering the effective amount of the unmodified RS type 2 potato starch preparation that is at least 60% resistant starch on the dosage regimen promotes a symbiotic or non-dysbiotic gut microbiome profile by reducing endogenous levels of members of the family Enterobacteriaceae in the gut microbiome of the individual.

15. The method according to claim 7 wherein administering the effective amount of the unmodified RS type 2 potato starch preparation that is at least 60% resistant starch on the dosage regimen promotes a symbiotic or non-dysbiotic gut microbiome profile by reducing endogenous levels of members of phylum Proteobacteria in the gut microbiome of the individual.

16. The method according to claim 7 wherein administering the effective amount of the unmodified RS type 2 potato starch preparation that is at least 60% resistant starch on the dosage regimen promotes a symbiotic or non-dysbiotic gut microbiome profile by reducing endogenous levels of *Escherichia* and *Shigella* in the gut microbiome of the individual.

17. The method according to claim 7 wherein administering the effective amount of the unmodified RS type 2 potato starch preparation that is at least 60% resistant starch on the dosage regimen promotes a symbiotic or non-dysbiotic gut microbiome profile by decreasing levels of endogenous B. dentum in the gut microbiome of the individual.

18. The method according to claim 7 wherein administering the effective amount of the unmodified RS type 2 potato starch preparation that is at least 60% resistant starch on the dosage regimen decreases need for stool softeners by the individual.

19. The method according to claim 3 wherein the individual is diagnosed with a dysbiotic gut microbiome by a method comprising:
  determining levels of bacteria of interest within the gut microbiome of the individual;
  determining levels of the bacteria of interest within the gut microbiome of a control individual; and
  comparing the populations;
  wherein if gut microbiome diversity of the individual and gut microbiome diversity of the control individual, the individual has a dysbiotic gut microbiome.

* * * * *